United States Patent [19]
Kay et al.

[11] Patent Number: 6,132,989
[45] Date of Patent: Oct. 17, 2000

[54] METHODS AND COMPOSITIONS FOR ENHANCED STABILITY OF NON-ADENOVIRAL DNA

[75] Inventors: Mark A. Kay; Andre Lieber, both of Seattle, Wash.

[73] Assignee: University of Washington, Seattle, Wash.

[21] Appl. No.: 08/972,657

[22] Filed: Nov. 18, 1997

Related U.S. Application Data

[63] Continuation-in-part of application No. 08/867,012, Jun. 2, 1997, abandoned.
[60] Provisional application No. 60/018,928, Jun. 3, 1996.
[51] Int. Cl.$^7$ ..................................................... C12N 15/00
[52] U.S. Cl. ........................ 435/69.1; 435/448; 435/455; 435/456; 435/320.1
[58] Field of Search ............................... 435/172.3, 69.1, 435/320.1, 370, 458, 235.1; 514/44; 536/23.1, 23.72, 29.1

[56] References Cited

U.S. PATENT DOCUMENTS

| | | | |
|---|---|---|---|
| 4,861,719 | 8/1989 | Miller | 435/236 |
| 4,959,317 | 9/1990 | Sauer | 435/462 |
| 5,124,263 | 6/1992 | Temin et al. | 435/349 |
| 5,219,740 | 6/1993 | Miller et al. | 435/69.6 |
| 5,399,346 | 3/1995 | Anderson et al. | 424/93.21 |
| 5,434,066 | 7/1995 | Bebee et al. | 435/475 |

FOREIGN PATENT DOCUMENTS

| | | |
|---|---|---|
| 0300422 | 1/1989 | European Pat. Off. . |
| WO 92/15694 | 9/1992 | WIPO . |
| WO 94/08026 | 4/1994 | WIPO . |
| WO 94/12649 | 6/1994 | WIPO . |
| WO 94/19460 | 9/1994 | WIPO . |
| WO 95/00655 | 1/1995 | WIPO . |
| WO 95/02697 | 1/1995 | WIPO . |
| WO 95/11984 | 5/1995 | WIPO . |
| WO 95/23867 | 9/1995 | WIPO . |
| WO 95/27071 | 10/1995 | WIPO . |
| WO 95/34671 | 12/1995 | WIPO . |

OTHER PUBLICATIONS

Angeletti and Engler, "Tyrosine kinase–dependent release of an adenovirus preterminal protein complex from the nuclear matrix," *J. Virol.* 70:3060–3067 (1996).

Anton and Graham, "Site–specific recombination mediated by an adenovirus vector expressing the cre recombinase protein: a molecular switch for control of gene expression" *J. Virol* 69:4600–4606 (1995).

Araki et al., "Site–specific recombinase, R, encoded by yeast plasmid pSR1" *J. Mol. Biol.* 225:25–37 (1992).

Fisher et al., "Transduction with recombinant adeno–associated virus for gene therapy is limited by leading–strand synthesis" *J. Virol.* 70:520–532 (1996).

Fredman and Engler, "Adenovirus precursor to terminal protein interacts with the nuclear matrix in vivo and in vitro," *J. Virol.* 67:3384–3395 (1993).

Gu et al., "Independent control of immunoglobulin switch recombination at individual switch regions evidenced through Cre–loxP–mediated gene targeting" *Cell* 73:1155–1164 (1993).

Hawley et al., "Versatile retroviral vectors for petential use in gene therapy," *Gene Therapy* 1:136–138 (1994).

Hodgson, C.P., "The vector void in gene therapy" *Biotechnology* 13:222–225 (1995).

Johnson et al., "Isolation of the gene encoding the hin recombinational enhancer binding protein" *Proc. Natl. Acad. Sci. USA* 85:3484–3488 (1988).

Kay et al., "Expression of human $\alpha_1$–antitrypsin in dogs after autologous transplantation of retroviral transduced hepatocytes" *Proc. Natl. Acad. Sci. USA* 89:89–93 (1992).

Kay et al., "Hepatic gene therapy: persistant expression of human $\alpha$1–antitrypsin in mice after direct gene delivery in vivo" *Hum .Gene Therapy* 3:641–647 (1992).

Kay et al., "In vivo gene therapy of hemophilia B: sustained partial correction in factor IX–deficient dogs" *Science* 262:117–119 (1993).

Kay et al., "In vivo Hepatic gene therapy: Complete albeit transient correction of Factor IX deficiency in hemophilia B dogs" *Proc. Natl. Acad. Sci. USA* 91:2353–2357 (1994).

Kay et al., "Therapeutic serum concentrations of human alpha$_1$–antitrypsin after adenoviral–mediated gene transfer into mouse hepatocytes" *Hepatology* 21:815–819 (1995).

Kay et al., "Long–term hepatic adenovirus–mediated gene expression in mice following CTLA4Ig administration" *Nature Genetics* 11:191–197 (1995).

Kochanek et al., "A new adenoviral vector for gene therapy: Replacement of all viral coding sequences with 28 kb of foreign DNA" *Am. J. Hu. Genetics* [abstract] 57(4): A244 (1995).

Ledley et al., "Retroviral mediated transfer and expression of human alpha 1–antitrypsin in cultured cells" *Gene* 61:113–118 (1987).

Li et al., "Assessment of recombinant adenoviral vectors for hepatic gene therapy" *Human Gene Therapy* 4:403–409 (1993).

(List continued on next page.)

*Primary Examiner*—Remy Yucel
*Attorney, Agent, or Firm*—Campbell & Flores LLP

[57] ABSTRACT

The invention provides compositions of a non-adenoviral vector containing a polynucleotide sequence encoding adenoviral pTP operationally linked domain. The invention also provides compositions of an adenoviral pTP binding domain. The invention also provides methods for increasing the expression of a polynucleotide by expressing the polynucleotide in a non-adenoviral vector containing an adenoviral pTP binding domain in the presence of adenoviral pTP. The invention additionally provides methods to increase expression of a heterologous polynucleotide in an individual by obtaining cells from the individual, genetically altering the cells to express a non-adenoviral vector containing an adenoviral pTP binding domain and a gene encoding pTP and readministering the genetically altered cells to the individual.

11 Claims, 6 Drawing Sheets

OTHER PUBLICATIONS

Marshall, E., "Gene therapy's growing pains" *Science* 269:1050–1055 (1995).

Mitani and Caskey, "Delivering therapeutic genes—matching approach and application" *Trends Biotechnol.* 11:162–166 (1993).

Mitani et al., "Rescue, propagation, and partial purification of a helper virus–dependent adenovirus vector" *Proc. Natl. Acad. Sci. USA* 92:3854–3858 (1995).

Naldini, et al., "In vivo gene delivery and stable transduction of nondividing cells by a lentiviral vector" *Science* 272:263–267 (1996).

O'Gorman et al., "Recombinase–mediated gene activation and site–specific integration in mammalian cells" *Science* 251:1351–1355 (1991).

Onouchi et al., "Visualization of site–specific recombination catalyzed by a recombinase from *Zygosaccharomyces rouxii* in *Arabidopsis thaliana* " *Mol. Gen. Genet.* 247:653–660 (1995).

Rosenfeld et al., "Adenovirus–mediated transfer of a recombinant α1–antitrypsin gene to the lung epithelium in vivo" *Science* 252:431–434 (1991).

Scaria et al., "Complementation of a human adenovirus early region 4 deletion mutant in 293 cells using adenovirus–polylysine–DNA complexes" *Gene Therapy* 2:295–298 (1995).

van der Vliet, *The molecular repertoire of adenoviruses* vol. 2, pp. 1–31 Doerfler and Böhm, eds. Springer–Verlag, Berlin (1995).

Webster et al., "Activation of adenovirus–coded protease and processing of preterminal protein" *J. Virol.* 68:7292–7300 (1994).

Orkin et al. Report and recommendation of the panel to assess the NIH investment in research on gene therapy, Dec. 1995.

Freidman, T. Scientific American, pp. 96–101, Jun. 1997.

Verma et al. Nature. vol. 389, pp. 239–242, Sep. 1997.

van der Vliet, P.C. The molecular repertoire of adenoviruses. vol. 2, pp. 1–31. Doerfler adn Bohm. eds. Springer–Verlag, Berlin, 1995.

Schaack et al., Genes and Development. vol. 4, pp. 1197–1208, 1990.

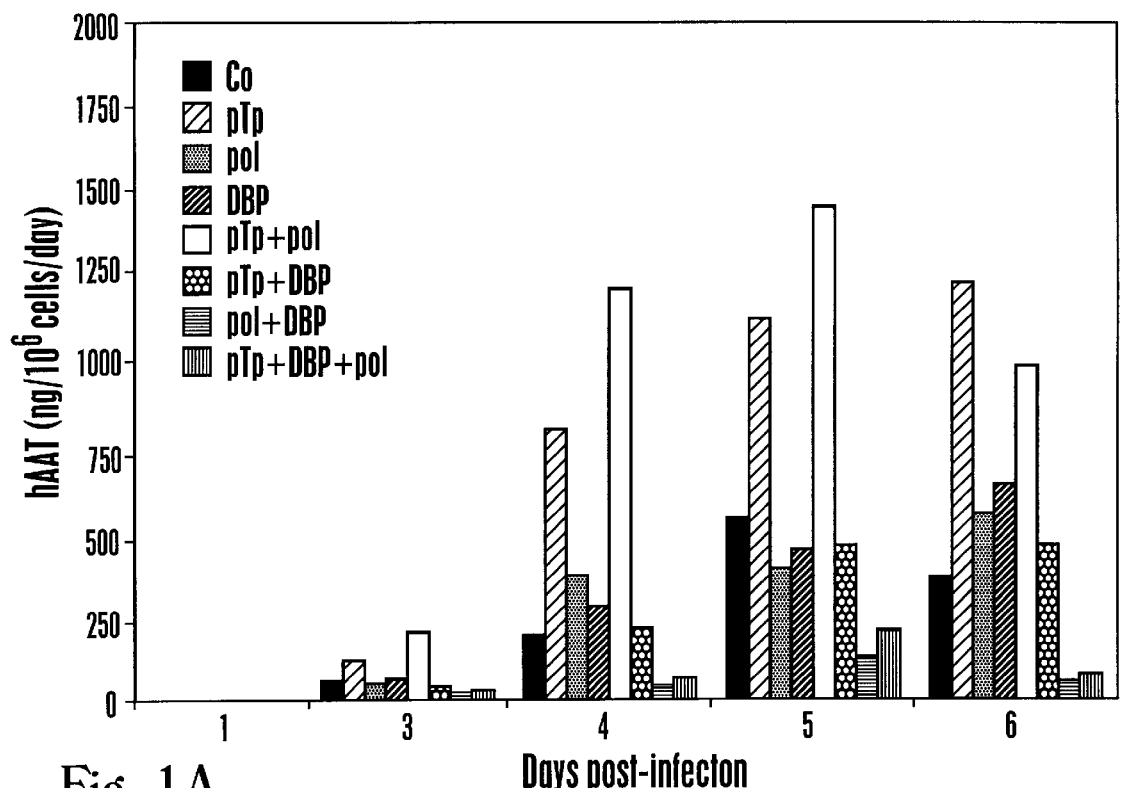
Fig. 1A
Fig. 1B
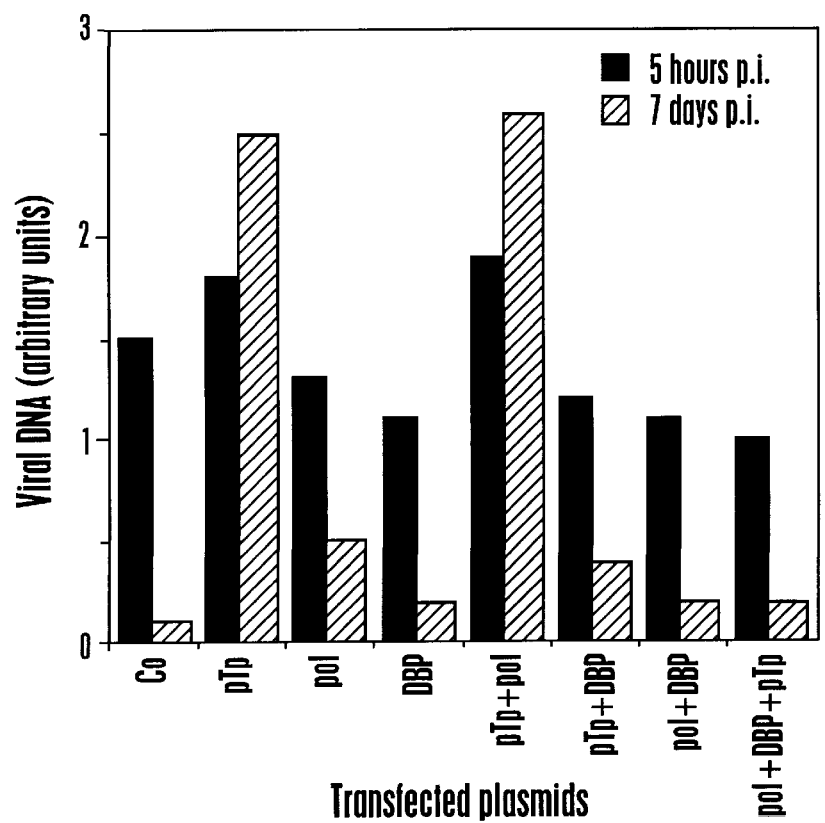

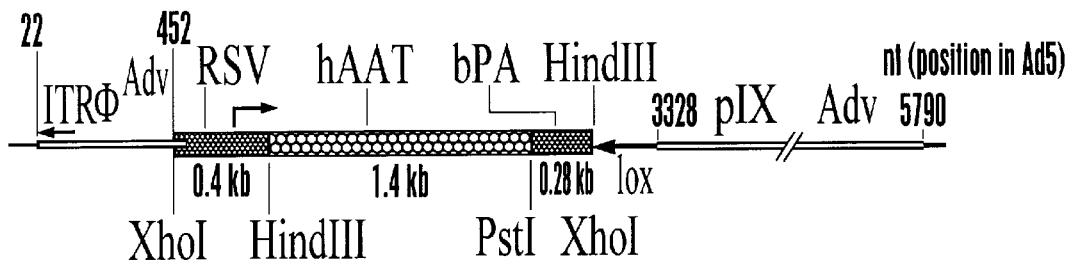
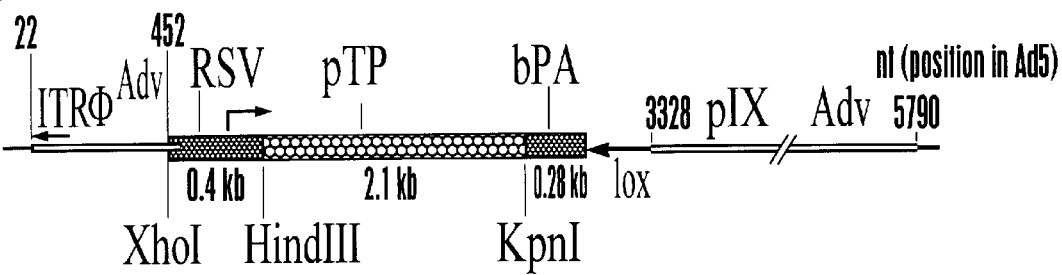
Fig. 2A
Fig. 2B
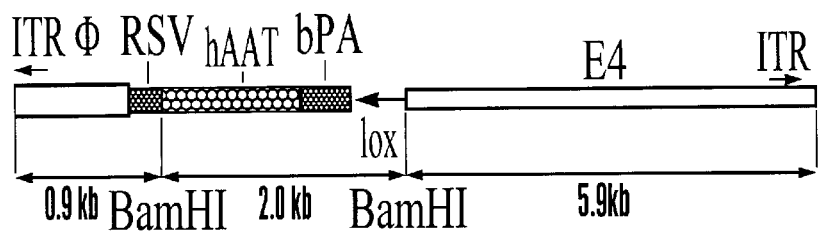
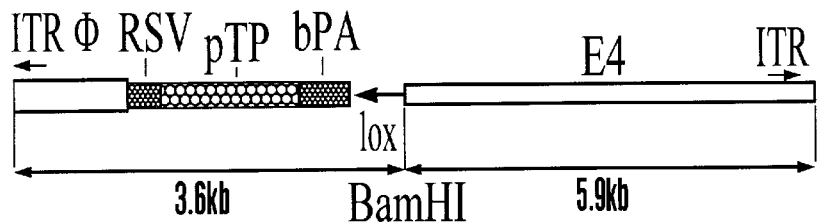

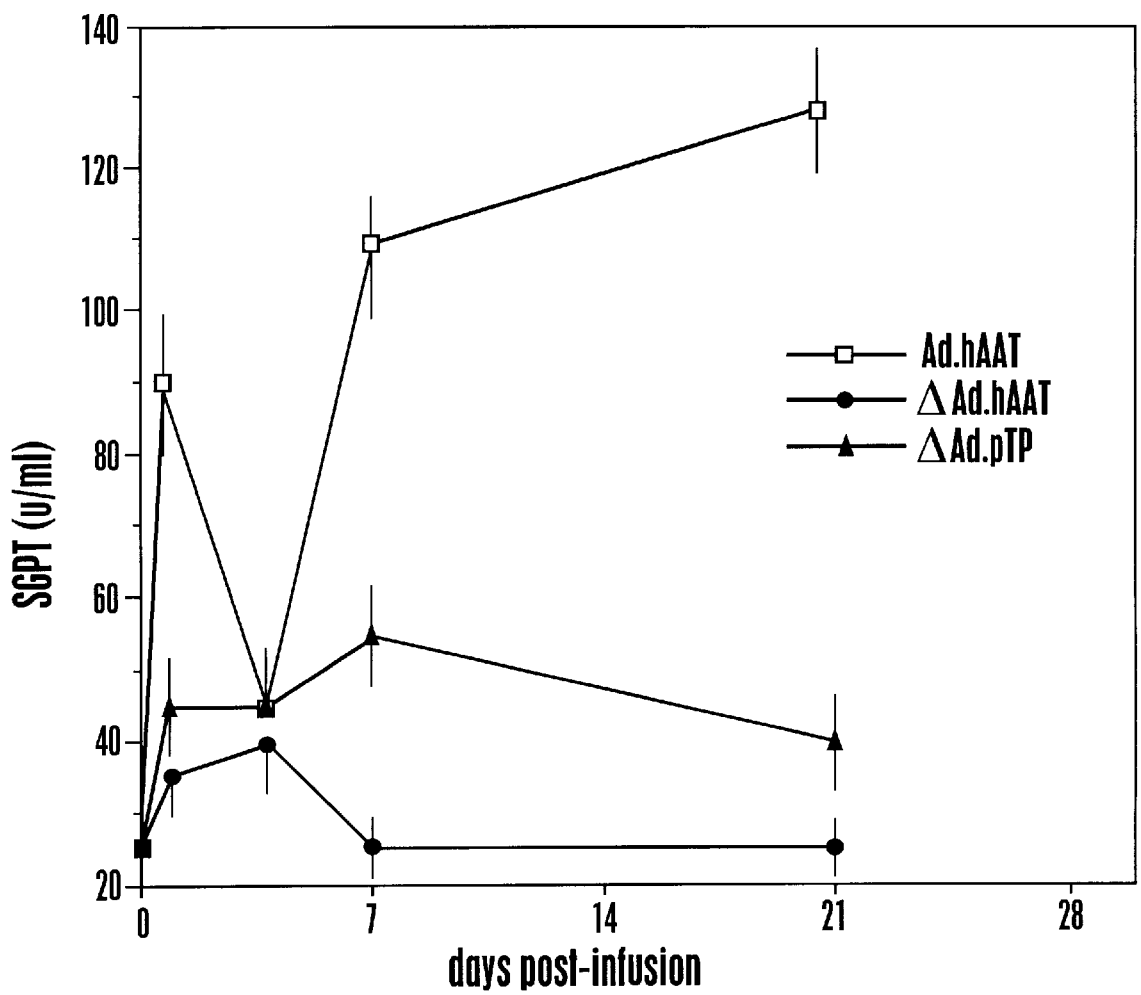
Fig. 5
Fig. 6
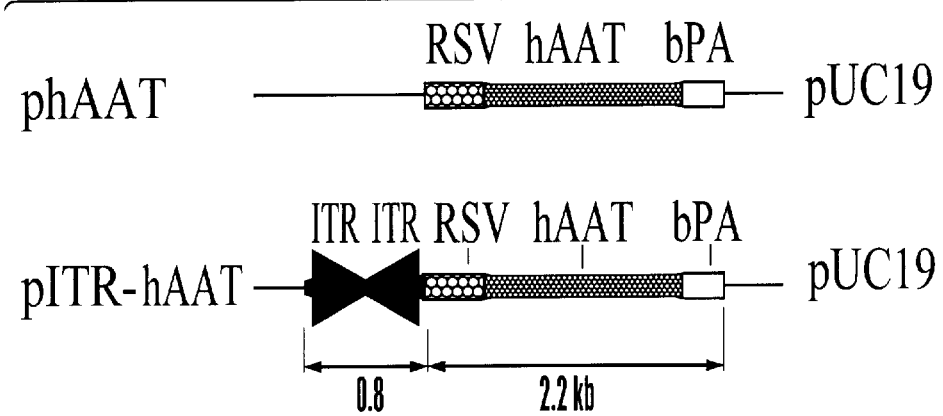

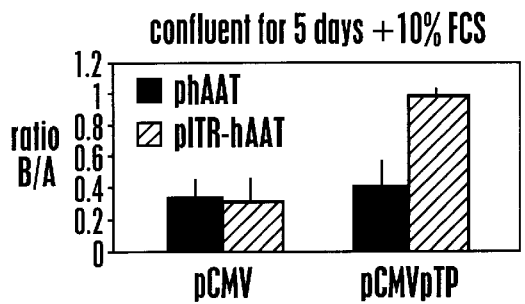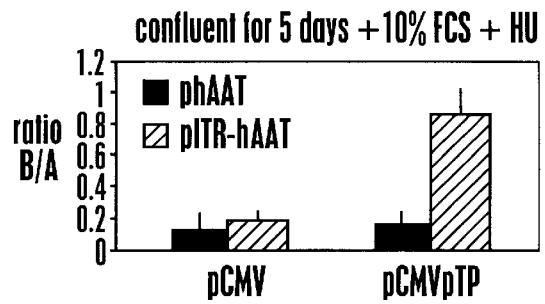
Fig. 7A    Fig. 7B
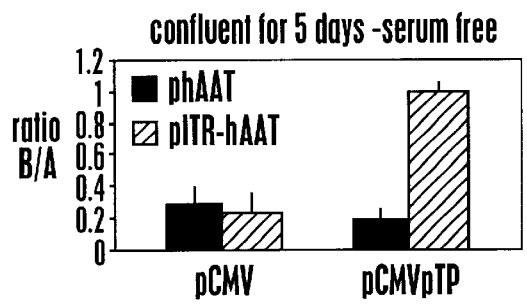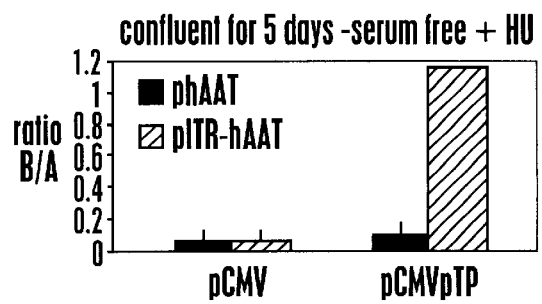
Fig. 7C    Fig. 7D
Fig. 8
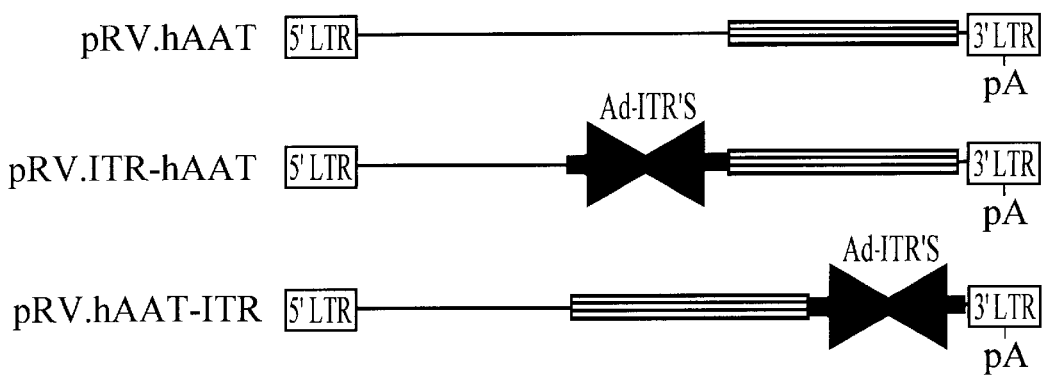

METHODS AND COMPOSITIONS FOR ENHANCED STABILITY OF NON-ADENOVIRAL DNA

This application is a continuation-in-part of U.S. Ser. No. 08/867,012, filed Jun. 2, 1997, now abandoned, which claims priority to United States Provisional Application NO. 60/018,928, filed Jun. 3, 1996, now abandoned, the entire contents of which is hereby incorporated by reference.

This invention was made with government support under grant number DK49022 awarded by the National Institutes of Health. The government has certain rights in the invention.

BACKGROUND OF THE INVENTION

The present invention relates generally to the field of gene therapy and more specifically to enhancing stability of vectors containing an expressible therapeutic gene.

A central challenge in gene therapy is delivering the therapeutic gene to the tissue site where it can be of benefit. Many pathological conditions have been identified that should be amenable to genetic therapy. Therapeutically relevant genes have been cloned and sequenced, and expression systems have been developed that should allow them to play a therapeutic role once inside the affected cells. However, clinical attempts at gene therapy have been largely disappointing.

SUMMARY OF THE INVENTION

The invention provides a non-adenoviral vector containing a polynucleotide sequence encoding adenoviral pTP operationally linked to expression elements and an adenoviral pTP binding domain. The invention also provides an adenoviral pTP and a non-adenoviral vector containing an adenoviral pTP binding domain. The invention also provides methods for increasing the expression of a polynucleotide by expressing the polynucleotide in a non-adenoviral vector containing an adenoviral pTP binding domain in the presence of adenoviral pTP. The invention additionally provides methods to increase expression of a heterologous polynucleotide in an individual by obtaining cells from the individual, genetically altering the cells to express a non-adenoviral vector containing an adenoviral pTP binding domain and a gene encoding pTP and readministering the genetically altered cells to the individual.

BRIEF DESCRIPTION OF THE DRAWINGS

FIGS. 1A and 1B show the effect of transient expression of the E2 proteins pTP, polymerase (pol) and DBP on the stability of ΔAd.hAAT in vitro. Part A shows the hAAT concentrations. Part B shows viral DNA.

FIGS. 2A and 2B show vectors used for generation of deleted vectors (part A) and the structure of ΔAd.hAAT and ΔAd.pTP (part B).

FIG. 5 shows SGPT levels in mice infused with first generation adenovirus hAAT, ΔAd.hAAT or ΔAd.pTP.

FIG. 6 shows phAAT and pITR-hAAT vectors.

FIG. 7 shows the effect of pTP on nuclear transport of vector DNA.

FIG. 8 shows retroviral vectors pRV.hAAT, pRV.ITR-hAAT and pRV.hAAT-ITR.

DETAILED DESCRIPTION OF THE INVENTION

Figure 3:
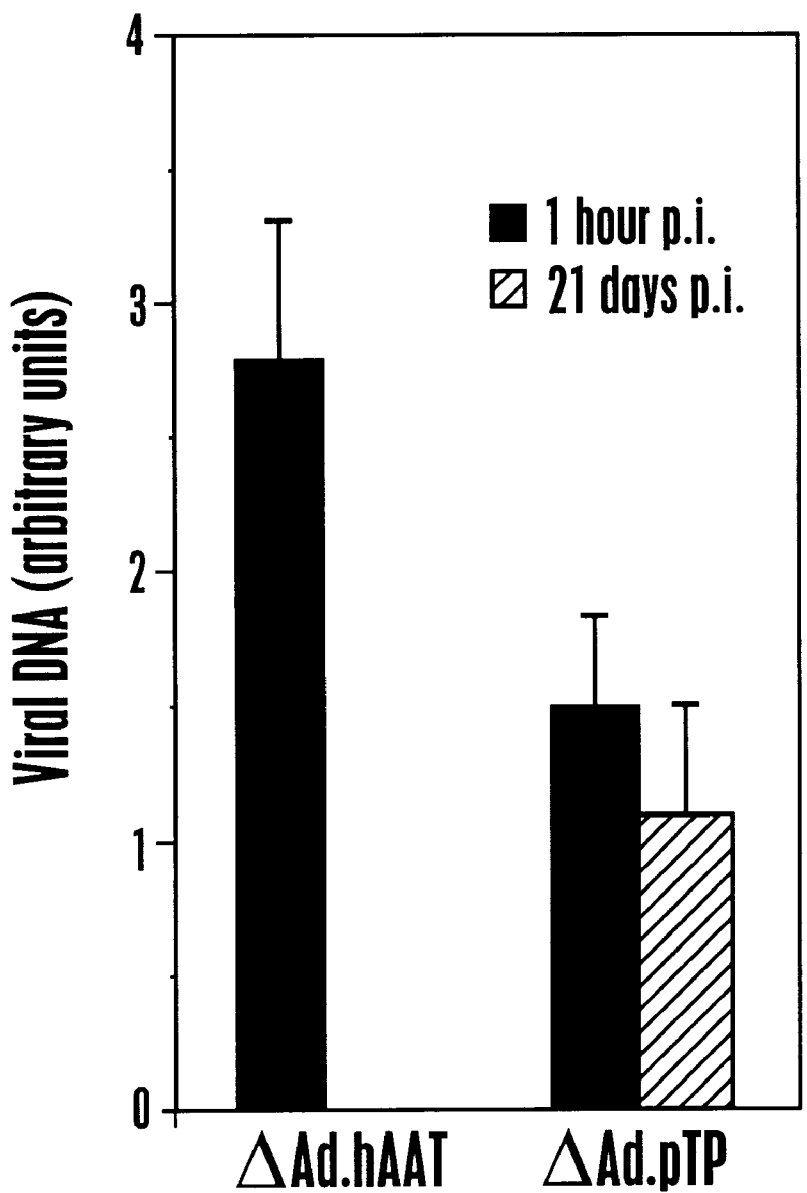
FIG. 3 shows analysis of viral DNA after transduction in vivo with ΔAd.hAAT and ΔAd.pTP.

The invention provides compositions and methods to enhance stability of vector DNA. The methods are applicable to the stabilization of vector DNA containing heterologous genes useful in gene therapy applications. Stabilization of vector DNA is advantageous since it can prolong the effectiveness of a gene therapy treatment.

The terms "polynucleotide" and "oligonucleotide" are used interchangeably, and refer to a polymeric form of nucleotides of any length, either deoxyribonucleotides or ribonucleotides, or analogs thereof. Included are genes and fragments thereof, exons, introns, messenger RNA (mRNA), transfer RNA, ribosomal RNA, ribozymes, cDNA, recombinant polynucleotides, branched polynucleotides, plasmids, vectors, isolated DNA and RNA, nucleic acid probes, and primers. A polynucleotide can comprise modified nucleotides, such as methylated nucleotides and nucleotide analogs; modifications can be imparted before or after assembly of the polymer. The sequence of nucleotides can also be interrupted by non-nucleotide components. The term polynucleotide, as used herein, refers interchangeably to double- and single-stranded molecules. Unless otherwise specified or required, any embodiment of the invention described herein that is a polynucleotide encompasses both a double-stranded form and each of two complementary single-stranded forms known or predicted to make up the double-stranded form.

A linear sequence of nucleotides is "essentially identical" to another linear sequence, if each sequence or its complement is capable of hybridizing with the other sequence or its complement to form stable duplexes, preferably at higher stringency. Sequences can hybridize even if some of the nucleotide residues do not precisely correspond or align, but sequences that correspond or align more closely are comparably more preferred. Generally, a polynucleotide region of about 25 residues is essentially identical to another region, if the sequences are at least about 85% identical; more preferably, they are at least about 90% identical; more preferably, they are at least about 95% identical; still more preferably, the sequences are 100% identical. Where gaps are required to align one sequence with another, the degree of scoring is calculated with respect to the longer sequence without penalty for gaps. Sequences that preserve the functionality of the polynucleotide or a polypeptide encoded thereby are more closely identical.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation can affect the frequency, speed, or specificity of the process, and can be enhancing or inhibitory in nature. Control elements are known in the art. For example, a promoter and an enhancer are two examples of control elements. A promoter is a DNA region capable under certain conditions of binding RNA polymerase and initiating transcription of a coding region usually located downstream (in the 3' direction) from the promoter.

A "suitable" control element is one capable of exerting its function in the intended environment. For example, a suitable promoter operatively linked to an encoding region and introduced into a host cell promotes transcription of the encoding region in the cell.

"Operatively linked" refers to a juxtaposition of genetic elements, wherein the elements are in a relationship permitting them to operate in the expected manner. For instance, a promoter is operatively linked to a coding region if the promoter helps initiate transcription of the coding sequence. There can be intervening residues between the promoter and coding region so long as this functional relationship is maintained.

An "expressible" gene is a polynucleotide with an encoding sequence, which is capable of producing the functional form of the encoded molecule in a particular cell. For a sequence encoding a polypeptide, the gene is capable of being transcribed and translated. For an anti-sense molecule, the gene is capable of producing replicate transcripts comprising anti-sense sequence. For a sequence encoding a ribozyme, the gene is capable of producing catalytic RNA.

"Recombinant", as applied to a polynucleotide, means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

As used herein, the term "ribozyme" means an RNA molecule having an enzymatic activity which is to cleave or splice other separate RNA molecules in a nucleotide base sequence specific manner. A catalytic or enzymatic RNA molecule is an RNA molecule which is complementary in a substrate binding region to a specific RNA plus or minus strand target, and also has enzymatic activity that is active to cleave or splice RNA in that target, thereby altering the target molecule.

A "vector" refers to a recombinant DNA or RNA plasmid or virus that comprises a heterologous polynucleotide to be delivered into a target cell, either in vitro or in vivo. The heterologous polynucleotide can comprise a sequence of interest in gene therapy, and can be in the form of an expression cassette. As used herein, a vector need not have an origin of replication or be capable of replication in the ultimate target cell, such as a cell which is the intended target for genetic therapy. In several embodiments of the invention, vectors are generated by a process that involves replication, but do not themselves replicate.

A "viral vector" is a vector comprising at least a portion of a viral genome, and also comprises a viral capsid or envelope. A viral vector is said to be "derived from" a particular virus or viral strain when it comprises at least a portion of the respective genome, capsid or envelope.

A "defective" viral vector is a vector that is normally incapable of undergoing replication, except in the presence of a helper virus, a coinfecting vector, or a trans-acting element in a cultured cell line. A defective viral vector can nevertheless be capable of penetrating a target cell and delivering a polynucleotide.

A "deleted" virus or viral vector is one comprising a polynucleotide from which a segment has been excised, for example, by site-specific recombination during replication.

An "essential virus function" is a function delivered to an infected cell via a viral genome which, if absent, prevents the occurrence of an essential step in the normal infectious cycle of the virus, particularly genomic replication, encapsidation, or envelopment. An essential virus function can be supplied, for example, by providing a polynucleotide having the function, or by providing a polynucleotide encoding a polynucleotide or polypeptide having the function.

A "viral particle" minimally comprises portions of the capsid of an encapsidated virus, or portions of the envelope of an enveloped virus. It can also optionally comprise a viral genome or fragment thereof, or other polynucleotide, inside the capsid or envelope.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. A site-specific recombination site that has been cloned into a genome of a virus or viral vector, wherein the genome of the virus does not naturally contain it, is a heterologous recombination site. When a polynucleotide with an encoding sequence for a recombinase is used to genetically alter a cell that does not normally express the recombinase, both the polynucleotide and the recombinase are heterologous to the cell.

An "expression cassette" is a heterologous polynucleotide introduced artificially into a plasmid, viral particle, or cell. It comprises an encoding region operatively linked to a control element that allows it to be transcribed in certain environments, such as in a cell which is the intended target of gene therapy.

"Genetic alteration" refers to a process wherein a genetic element is introduced into a cell other than by mitosis or meiosis. The element can be heterologous to the cell, or it can be an additional copy or improved version of an element already present in the cell. Genetic alteration can be effected, for example, by transfecting a cell with a recombinant plasmid or other polynucleotide through any process known in the art, such as electroporation, calcium phosphate precipitation, or contacting with a polynucleotide-liposome complex. Genetic alteration can also be effected, for example, by transduction or infection with a DNA or RNA virus or viral vector.

A cell is said to be "inheritably altered" if a genetic alteration is introduced which is inheritable by progeny of the altered cell. Preferably, the genetic element is introduced into a chromosome or mini-chromosome in the cell; but any alteration that changes the phenotype and/or genotype of the cell and its progeny is included in this term.

"Efficiency" when used in describing a method for producing a viral vector refers to the number of such vectors produced per cell.

The terms "polypeptide", "peptide" and "protein" are used interchangeably herein to refer to polymers of amino acids of any length. The polymer can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation.

A "fusion polypeptide" is a polypeptide comprising regions in a different position in the sequence than occurs in nature. The regions can normally exist in separate proteins and are brought together in the fusion polypeptide; or they can normally exist in the same protein but are placed in a new arrangement in the fusion polypeptide.

"$\alpha_1$-antitrypsin", "Factor IX", "integrase", "replicase", and other proteins, when discussed in the context of gene therapy and the vector constructs therefor, refer to the respective intact polypeptide, or any fragment or genetically engineered derivative thereof, that retains the desired biochemical function of the intact protein.

An "immunogenic" compound is a compound capable of stimulating production of a specific immunological response when administered to a suitable host, usually a mammal. This includes administration as part of a composition, such as one comprising a viral particle. The immunological response can be either cellular (cytotoxic or inflammatory) or humoral, or any combination thereof.

A "cell line" or "cell culture" denotes higher eukaryotic cells grown or maintained in vitro. It is understood that the progeny of a cell can not be completely identical (either morphologically, genotypically, or phenotypically) to the parent cell. "Culturing" a cell means maintaining or propagating the cell in vitro.

A "host cell" denotes a eukaryotic cell has been genetically altered, or is capable of being genetically altered by administration of an exogenous polynucleotide, such as a bacterial plasmid or recombinant vector. When referring to genetically altered cells, the term refers both to the originally altered cell and to the progeny thereof.

An "isolated" virus, polynucleotide, polypeptide, or other substance refers to a preparation of the substance devoid of at least some of the other components that can also be present where the substance or a similar substance naturally occurs or is initially prepared from. Thus, for example, an isolated substance can be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred.

A functional biological component, such as a viral vector or an expression cassette, is said to be "specific" or "selective" if it is capable of exerting a function upon the intended target more frequently, more rapidly, or with greater duration than upon alternative targets. For viral particles and vectors, the function can be an ability to penetrate, infect, or transduce particular cells in preference to other cells. Specificity can be imparted, for example, by the ability of the vector to preferentially accumulate near the target cell, or a particular susceptibility of the target cell to the vector. An expression cassette can be specific for a particular cell type, for example, if it comprises a promoter which promotes transcription more actively in the target cell than in other cells.

"Targeting" is the process by which a composition such as a vector is permitted to accumulate in a particular locale in greater preference over other locales than would otherwise be the case. This can be accomplished by providing the compound or complex with a component, called a "tissue targeting component" or "targeting component" that enhances the accumulation of the composition with which it is associated at certain tissue sites in preference to others when administered to an intact animal, or enhances the accumulation of the composition in certain cell types in an in vitro culture.

An "individual" refers to vertebrates, particularly members of a mammalian species, such as domestic animals, sports animals, and primates, including humans.

"Treatment" of an individual or a cell is any type of intervention in an attempt to alter the natural course of the individual or cell at the time the treatment is initiated. For example, treatment of an individual can be undertaken to decrease or limit the pathology caused by any pathological condition, including (but not limited to) an inherited or induced genetic deficiency, infection by a viral, bacterial, or parasitic organism, a neoplastic or aplastic condition, or an immune system disfunction such as autoimmunity or immunosuppression. Treatment includes (but is not limited to) administration of a composition, such as a pharmaceutical composition, and administration of compatible cells that have been treated with a composition. Treatment can be performed either prophylactically or therapeutically; that is, either prior or subsequent to the initiation of a pathologic event or contact with an etiologic agent.

The invention provides non-adenoviral vector containing a polynucleotide sequence encoding adenoviral pTP operationally linked to expression elements and an adenoviral pTP binding domain.

The adenoviral pTP and vectors containing pTP binding domains of the invention provide increased stability to the vectors, thereby allowing heterologous polynucleotides to be expressed for longer periods of time. Deleted adenoviruses lacking the genes for immunogenic viral proteins encoded in the E2 and corresponding late region were generated. The mini-vector deleted for 33 kb of viral DNA and constituting a final size of 9 kb can be produced at high titers using a technique based on cre-lox recombination. The deleted virus transduced hepatocytes in vivo efficiently after intravenous infusion and without associated toxicity. However, transgene expression was transient due to instability of the vector genome in the nucleus of transduced cells. As disclosed herein, the deleted vector can be stabilized in trans by co-infection of an equal amount of first-generation adenovirus, suggesting that proteins encoded in the deleted region are needed for genome stabilization (see Example I).

The deleted region includes the pIX and E2 expression units. Protein IX is a minor structural protein while the E2 proteins are involved in viral DNA replication. Three of the major E2 mRNAs are generated by postranscriptional processing of a common precursor producing the E2a gene product, DBP (72 kDa), and the two E2b products, pTP (precursor terminal protein) (80 kDa) and the viral DNA polymerase (pol) (140 kDa). The region corresponding to E2 on the other DNA strand contains the major late promoter and the L1–L4 RNA family including penton (protein III/IIIa), hexon (II), and core proteins (VII, VI, VIII).

Nuclear-localized E2 proteins pTP, pol and DBP were analyzed with respect to their potential DNA stabilizing activity. The respective functions of these proteins during the life cycle of adenovirus infection are well studied. DBP binds cooperatively ssDNA synthesized during replication by forming a protein chain that is winded around the DNA. DBP influences all stages of replication by facilitating duplex unwinding and inhibition of intramolecular renaturation between complementary ends of ssDNA. After forming the final double-stranded replication product, DBP rapidly dissociates from the viral genome.

The pTP expressed early from the transduced parental viral DNA binds as heterodimer with pol within the origin found on each end of the linear genome within the ITR's. pTP is then covalently linked to dCTP, providing a free 3-hydroxyl group to begin the synthesis of a daughter DNA. pTP serves as the site of primary attachment of the viral DNA to specific protein(s) in the nuclear matrix forming replicative complexes (Angeletti et al., *J. Virol* 70:3060–3067 (1996); Fredmand and Engler, *J. Virol.*

67:3384–3395 (1993)). It is thought that the nuclear matrix facilitates adenovirus replication by providing structural support, fixing the ends of the replicating genomes, and/or by concentrating viral or cellular replication factors/enzymes (Pronk and van der Vliet, *Nucl. Acids Res.* 21:2293–2300 (1993)). pTP alone or in association with the nuclear matrix functions in the transactivation of viral promoters, in retaining viral DNA in the nucleus, and in protection from endonucleases (Webster et al., *J. Virol.* 68:7292–7300 (1994)). Late in infection, pTP is proteolytically cleaved by the viral proteases generating the 55 kD terminal protein (TP). Conversion of pTP to TP completes the process of DNA replication and releases the adenoviral genome from the nuclear matrix. TP-bound viral DNA is then packaged into capsids. After transduction, TP-DNA is transported to the nucleus employing the TP-nuclear localization signal, where it serves as a template for early transcription. Because only two copies of pTP/pol per genome are required during viral replication, the amount of pm ad pol produced is very low compared with the E2a product, DBP, despite the use of the same E2a promoter.

The coexpression of pTP, pol, or DBP individually or in combination was investigated to determine if they stabilized the deleted adenovirus in vitro (see Examples I–IV). As described herein, coexpression of the adenoviral pTP from the vector or in trans stabilized an adenoviral mini-genome in vitro and in vivo without evidence of cellular toxicity. A first generation adenovirus expressing pTP was found to enhance in trans the stability of an adenoviral mini-vector deleted of the E2 region containing pTP (see Example I). Expression of pTP from vector rather than from an adenovirus that naturally expressed pTP also resulted in stabilization of vector DNA in trans and in cis (see Examples II and III). Expression of pTP was also found to not be toxic in mice transduced with a deleted adenoviral vector containing the pTP gene (see Example VI).

The invention provides adenoviral pTP and a non-adenoviral vector containing an adenoviral pTP binding domain. The invention also provides methods for increasing the expression of a polynucleotide by expressing the polynucleotide in a non-adenoviral vector containing an adenoviral pTP binding domain in the presence of adenoviral pTP.

The invention also provides methods for using pTP to stabilize non-adenoviral vectors containing a binding site for pTP such as an adenovirus ITR, to achieve enhanced of a heterologous polynucleotide. The non-adenoviral vectors include viral DNA such as retroviral DNA, herpesviral DNA, poxviral DNA or any viral DNA that allows expression of the heterologous polynucleotide of interest. Representative retroviral vectors suitable for use in the present invention are described, for example, in U.S. Pat. Nos. 4,861,719, 5,124,263 and 5,219,740, Kay et al., *Hum. Gene. Ther.* 3:641–647 (1992) and Kay et al., *Science* 262:117–119 (1993). Other vectors can also be employed, particularly to introduce polynucleotides into cells by ex vivo methods. Such other vectors include, for example, DNA vectors, pseudotype retroviral vectors, adeno-associated virus, gibbon ape leukemia vector, VSV-G (see WO 94/29440), VL30 vectors, liposome mediated vectors, and the like. The vectors contain suitable control elements operationally linked to a heterologous polynucleotide that allow expression of the heterologous polynucleotide in the target cell or tissue of interest.

The vector can be introduced into a target cell or target tissue of an organism by various means that allow uptake of the vector into the appropriate target cell of interest and which allows expression of a heterologous polynucleotide. One means of delivering a vector to a target cell utilizes viral vectors and transduction of target cells using infectious viral particles containing a viral vector. Other means of delivering a vector to a target cell are also available and include delivery by an appropriate delivery vehicle such as a liposome, a controlled release vehicle, by use of iontophoresis, electroporation or ion paired molecules, or covalently attached adducts, and other pharmacologically acceptable methods of delivery. Preferably a carrier provides a means to accumulate the vector at the target site. The delivery vehicle can be designed to serve as a slow release reservoir or to deliver its contents directly to the target cell. Examples of delivery vehicles include liposomes, hydrogels, cyclodextrins, biodegradable nanocapsules, and bioadhesive microspheres. Liposomes can be targeted to the cells or tissue of interest.

Vectors of the present invention also contain a binding domain for pTP. A pTP binding domain is found, for example, in the adenoviral ITR. Therefore, inclusion of one or more adenoviral ITRs in the vector provides a pTP binding domain. However, the entire adenoviral ITR need not be present on the vector, only that portion which constitutes a functional pTP binding domain. For example, the 18 bp nucleotide sequence identified as a pTP binding domain can be used in the vector as a pTP binding domain (van der Vliet, p. 1–31 in *The Molecular Repertoire of Adenoviruses,* Vol. 2, Doerfler and Boehm, eds. Springer-Verlag, Berlin (1995)). The pTP binding domain can be present in the vector as a monomer or as multimers. The number and orientation of pTP binding domains, either as an adenoviral ITR or an 18 bp pTP binding domain, can be readily determined by those skilled in the art by introducing various numbers of pTP binding domains in various combinations or orientation into a vector and testing the effect of these various pTP binding domain combinations on vector stability in the presence of pTP. A desirable combination of numbers and orientation of pTP binding domains is one that is at least as effective at stabilizing the vector as is found with a single adenoviral ITR.

The invention also provides methods for introducing pTP into the cells or tissues of interest such that pTP is expressed and available for binding to the vector containing a pTP binding site. The introduction of pTP into the cell of interest can be accomplished by introducing DNA containing the pTP gene under the control of transcriptional regulatory elements allowing expression of pTP in the cell or tissue of interest. The pTP gene can be provided in cis on the same vector as the heterologous polynucleotide of interest, or can be provided in trans on a different DNA vector. If the pTP gene and the heterologous gene are located on different vectors, the two vectors can be introduced into the cells of interest simultaneously or the vectors can be introduced into the cells sequentially. The pTP gene can also be modified to incorporate changes in the third base of a codon so that the nucleotide sequence of the pTP gene differs from the native pTP gene but still encodes a polynucleotide identical to native pTP. Such codon changes serve to minimize homologous recombination of pTP with other pTP genes that are present in vectors or integrated into the host genome. In addition to the adenoviral 2 encoded pTP, pTP genes and corresponding encoded pTP polypeptides from other adenovirus strains can also be used.

The introduction of isolated pTP into cells can also be accomplished by heterologously expressing pTP outside of the cell of interest, isolating the protein, and introducing the isolated protein into the cell or tissue of interest. The pTP protein can be isolated by any of a variety of means known to those skilled in the art including subcellular fractionation and various chromatographic techniques such as affinity, ion exchange and hydrophobic chromatography. Any method of isolation can be used to enrich for a pTP fraction so long as the pTP activity of stabilizing DNA containing a pTP binding site is retained. The isolation of the pTP preparation is considered to be sufficient if it allows introduction of pTP into appropriate target cells of an organism to achieve the desired effect of stabilizing DNA containing a pTP binding site without causing harmful side effects. A more pure preparation of pTP can be advantageous in that a higher concentration of pTP can be achieved as well as possible improved efficacy. Delivery of isolated pTP can be carried out by co-packaging isolated pTP into virions such as vesicular stomatitis virus (Liu et al., *J. Virol.* 70:2497–2502 (1996); Schnell et al., *Proc. Natl. Acad. Sci.* USA 93:11359–11365 (1996)). Alternatively, isolated pTP can be delivered into a target cell or tissue by the liposome mediated delivery methods described above. The delivery of pTP to the target cell or tissue of interest can be provided either simultaneously or separately with the vector of interest.

The invention additionally provides methods of increasing the expression of a heterologous polynucleotide in an individual by obtaining cells from an individual, genetically altering the cells to express a non-adenoviral vector containing an adenoviral pTP binding domain and a gene encoding pTP and readministering the genetically altered cells to the individual.

For purposes of gene therapy, the vector will typically contain a heterologous polynucleotide of interest containing a region with a beneficial function. The polynucleotide can be directly therapeutic, but more usually will be transcribed into a therapeutic polynucleotide, such as a ribozyme or anti-sense strand, or transcribed and translated into a therapeutic polypeptide. Alternatively or in addition, the polynucleotide can provide a function that is not directly therapeutic, but which permits or facilitates another composition or agent to exert a therapeutic effect. The heterologous polynucleotide, if included, will be of sufficient length to provide the desired function or encoding sequence, and will generally be at least about 100 base pairs long, more usually at least about 200 base pairs, frequently at least about 500 base pairs, often at least about 2 kilobases, and on some occasions about 5 kilobases or more.

Where transcription of the heterologous polynucleotide is desired in the intended target cell, it can be placed under control of a promoter region of the vector, for example, by splicing downstream from the promoter site. Alternatively, it can be introduced into the vector with its own promoter. The promoter used with a particular encoding region can be the same as the one with which it is operatively linked in nature, or the promoter and encoding region can be linked by genetic manipulation. Enhancer elements can also be included.

Various types of promoters and enhancers are suitable for use with this invention. Promoters and enhancers can be constitutive or inducible. Constitutive promoters provide an ongoing level of gene transcription, and are preferred when it is desired that the therapeutic polynucleotide be expressed on an ongoing basis. Inducible promoters generally exhibit low activity in the absence of the inducer, and are up-regulated in the presence of the inducer. They can be preferred when expression is desired only at certain times or at certain locations, or when it is desirable to titrate the level of expression using an inducing agent. Inducible promoters known in the art include heavy metal ion inducible promoters (such as the mouse mammary tumor virus (MMTV) promoter or growth hormone promoter), and the promoters from T7 phase which are active in the presence of T7 RNA polymerase. Promoters and enhancers can also be tissue-specific: that is, they exhibit their activity only in certain cell types, presumably due to gene regulatory elements found uniquely in those cells. Some examples of tissue specific promoters that can be used in the practice of the invention include the albumin promoter (for expression in the liver) or the surfactin promoter (for expression in the lung). In another example, the muscle creatine kinase enhancer combined with the human cytomegalovirus immediate early promoter can be used for expression of an encoding region in muscle tissue.

Further illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include those from MT II, collagenase, stromelysin, SV40, murine MX Gene, $\alpha_2$-Macroglobulin, MHC Class I gene H-2kb, HSP70, proliferin, Tumor Necrosis Factor or Thyroid Stimulating Hormone I gene. Preferred promoters for use in this invention include the human CMV promoter, the HSV tk promoter, the T-lymphocyte specific Ick promoter. Particularly preferred for inclusion in the therapeutic polynucleotide cassette are the phosphoglycerate kinase (PGK) promoter, and especially the RSV-LTR promoter.

Where translation is also desired in the intended target cell, the heterologous polynucleotide will also comprise control elements used in translation such as a ribosome binding site and a polyadenylation signal. Suitable polyadenylation signals include the tk poly-A signal and the bovine poly-A signal (bPA).

Accordingly, the heterologous polynucleotide generally contains at least one encoding region operatively linked to a suitable promoter and optionally an enhancer and/or an operatively linked poly-A signal. The heterologous polynucleotide can contain one encoding region or more than one encoding regions under the control of the same or different promoters. The entire unit, containing a combination of control elements and encoding regions is referred to as an expression cassette.

Certain elements of the viral genome can be required for a delivered therapeutic polynucleotide to exert its effect. Such elements are referred to herein as "effector elements". For example, effector elements can stabilize and increase persistence of the therapeutic polynucleotide in the target cell, or provide a low level of replication or other functional activity that is required to initiate a process that leads to expression of the therapeutic polynucleotide. Effector elements can exert their effect via an encoded protein or protein fragment, although other mechanisms are possible.

In the adenovirus system, elements contained within the E2 region stabilize vector DNA in the host cell and promote expression of heterologous expression cassettes. The responsible elements are likely to act during initiation of the replicative phase of the virus, not in packaging. Effector elements potentially useful for therapeutic gene expression in an adenovirus vector include the 72-kDa DNA-binding protein, the 80-kDa precursor terminal protein, and the 140-kDa DNA polymerase, and other minor E2 proteins. Effector elements in lentiviruses include, for example, Vpr and matrix protein (MA).

In the adenoviral system, for example, encoded on the opposite strand of the E2 region are certain late-phase proteins involved in packaging. Accordingly, adenovirus vectors of the invention generally are those where E2 is in an excisable region but where another copy of the DNA-stabilizing elements of E2 are cloned. For example, the precursor terminal protein, pTP, binds to the adenoviral origin of replication and functions to stabilize adenoviral DNA. This function of pTP can also involve interactions with DNA polymerase. Thus, the polynucleotides encoding these two gene products are specific examples of effector elements within the adenoviral E2 region. The effector element or elements are placed in operative linkage with a homologous or heterologous promoter such that the effector elements exert their stabilizing function without allowing other gene fragments, for example, late gene encoding regions on the opposite strand, to exert their function. The reintroduced effector elements can be contained in the same expression cassette with the therapeutic polynucleotide. Preferably, they are provided as a separate operative unit under control of a different promoter, since the desired levels of expression required are typically expected to be lower. Alternatively, such elements can be provided in trans. In one embodiment, the promoter is 500 bp of the E2 promoter.

A variety of heterologous polynucleotides are suitable for use in the present invention. The heterologous polynucleotide can be of direct therapeutic benefit, or it can provide a function that facilitates the action of a therapeutic polynucleotide from another source. The function of the heterologous polynucleotide can include supplementing or replacing expression of a host gene, conferring novel biological functions, suppressing tumors, selective cell killing, suppressing expression by antisense therapy, delivering ribozymes and delivering components of other viral systems.

Supplementing or replacing expression of a host gene is useful when certain pathological conditions arise from abnormally low levels of expression of a particular gene. The low expression level can arise due to an inherited or induced genetic deficiency, or expression can be suppressed by an infection, an environmental toxin, or by autoimmunity. In addition, certain conditions such as infection or anemia can benefit from expression of a cytokine or growth factor at supernormal levels.

Accordingly, useful therapeutic polynucleotides for inclusion in the vectors of this invention include encoding regions for a therapeutic protein such as coagulation factors (especially Factor VIII, Factor IX and Factor VII), $\alpha_1$-antitrypsin, cystic fibrosis transmembrane conductance regulator (CFTR), erythropoietin, calcitonin, growth hormone, insulin, low density lipoprotein, apolipoprotein E, IL-2 receptor and its antagonists, superoxide dismutase, immune response modifiers, parathyroid hormone, the interferons (IFN alpha, beta, or gamma), tumor necrosis factors, nerve growth factors, glucocerebrosidase, interleukins (IL) 1 to 15, and colony stimulating factors of various kinds including granulocyte colony stimulating factor (G-CSF), granulocyte macrophage colony stimulating factor (GM-CSF), macrophage stimulating factor (M-CSF), fibroblast growth factor (FGF), platelet-derived growth factor (PDGF), adenosine deaminase, insulin-like growth factors (IGF-1 and IGF-2), and megakaryocyte promoting ligand (MPL, or thrombopoietin).

Gene therapy can be used to introduced novel biological functions to certain cells by conferring to the cells the ability to express proteins not usually in their repertory. For example, circulating cells can be provided with adhesion proteins to alter their migration patterns. Quiescent cells can be provided with receptors for growth factors like EGF, so that replication can be induced with the corresponding hormone. Immune cells like T cells can be provided with novel fusion proteins that facilitate interactions with other cells. Genes encoding enzyme, epitope, or hybridization markers can be used to monitor the state of disease, the longevity of undesirable cells in the diseased tissue, or the longevity of the modified or transplanted cells in the diseased tissue. Cells can be rendered amphotropic for other viral vectors by delivering an expression cassette for a functional amphotropic receptor (Lieber et al., *Hum. Gene Ther.* 6:5–11 (1995)). In another example, histocompatibility phenotype of a tissue can be altered by providing a polynucleotide encoding the desired class I or class II antigen.

Suppressing tumors is desirable when suitable genes for tumor therapy, including proteins effective in regulating the cell cycle and implicated in tumor suppression, such as p53 (Roth et al., WO 95/28948), retinoblastoma (RB, p110$^{RB}$, p56$^{RB}$) (Zhang et al., WO 95/11984), or mitosin. Also included are proteins effective in inducing cell death, such as the conditional suicide gene thymidine kinase, which is used in conjunction with a thymidine kinase metabolite. Other tumor suppressor genes include p16 protein, p21 protein, Wilm's tumor WT1 protein, h-NUC, or colon carcinoma DCC protein.

Selective cell killing is useful when it is clinically desirable to selectively kill a certain cell population in an affected individual. Target cells can include virally infected cells, tumor cells, and cells no longer performing an important physiological function. Removing the cells can allow healthy cells to grow back. This approach can also be useful to induce proliferation in a tissue that normally does not proliferate in the adult. For example, killing cells with a vector containing a toxic element can be a useful adjuvant to forms of therapy mediated by agents that need proliferation to exert their effect. An example of an agent of this kind is a retroviral vector.

Suitable toxins include the cytotoxic domain of bacterial toxins such as Pseudomonas exotoxin A, diphtheria toxin, cholera toxin, shiga and shiga-like toxin, ribosome inactivating toxins derived from plants and fungi (e.g., ricin), hepatocyte growth factor, and other toxic polypeptides (Frankel, *Genetically Engineered Toxins,* Marcel Dekker, Inc. (1992)). Substances that are hepatotoxic include tissue-type plasminogen activator (tPA), and urokinase-type plasminogen activator (uPA), particularly uPA that has been modified to prevent secretion from the cell (see commonly owned U.S. Pat. No. 5,980,866, issued Nov. 9, 1999 which is incorporated herein by reference).

Suppressing expression by antisense therapy is useful to provide a therapeutic polynucleotide that interferes with either transcription or translation of a particular gene to attenuate the level of expression of the endogenous gene. The construct is designed so that the polynucleotide sequence operatively linked to the promoter is complementary to the sequence of the corresponding gene, or a transcript thereof. Thus, once integrated into the cellular genome, the transcript of the administered polynucleotide will be complementary to the transcript of the gene, and capable of hybridizing with it. This approach is known as anti-sense therapy. This can be used for the suppression of an undesirable phenotype, such as the product of a gene amplified or overexpressed during the course of a malignancy, or a gene introduced during the course of a microbial infection.

Delivering ribozymes is useful for treating any pathological condition that involves the formation of RNA transcripts or genetic elements during the course of the pathology. The purpose of administering the ribozyme is to enhance the destruction of the undesirable RNA and thereby ameliorate the pathology of the disease. Such conditions include viral infection, where undesirable RNA includes transcripts and genetic copies encoding essential viral functions; cancerous conditions, where undesirable RNA includes transcripts for tumor-associated markers and growth enhancers; and autoreactive conditions, where undesirable RNA includes transcripts encoding pathologic self-recognition or the sequelae thereof.

Each ribozyme molecule contains a catalytically active segment, capable of cleaving a target polynucleotide such as RNA. The ribozyme also contains flanking sequences having a nucleotide sequence that serves to anneal the ribozyme to the RNA in a site-specific manner. Only an amount of complementarily sufficient to form a duplex with the target RNA and to allow the catalytically active segment of the ribozyme to cleave at the target sites is necessary.

Preferably, the enzymatic RNA molecule is formed in a hammerhead motif (Rossi et al., AIDS Res. Hum. Retrovir. 8:183 (1992)), but the ribozyme can also be formed in the motif of a hairpin (Hampel and Tritz, Biochemistry 28:4929 (1989); Hampel et al., Nucl. Acids Res. 18:299 (1990)), hepatitis delta virus motif (Perotta et al., Biochemistry 31:16 (1992)), group I intron motif (Cech et al., U.S. Pat. No. 4,987,071), or RNAse P RNA in association with an RNA guide sequence (Guerrier-Takada et al., Cell 35:849 (1983)). The type of ribozyme will affect the site of cleavage in a target RNA molecule. For example, when the ribozyme is of the hammerhead type, the substrate cleavage site is immediately 3' to the sequence NUH. Different types of ribozymes can be used to achieve a desired cleavage on the target molecule.

The flanking sequences upstream and downstream of the ribozyme catalytic site provide the specificity for the RNA target. They should be complementary to either the plus or minus strand of the target RNA, downstream or upstream from the intended cleavage site. They can comprise segments of any length that effectively impart the desired degree of targeting specificity for the ribozyme. Typically, the flanking sequences are about 4–24 nucleotides, and more typically they are about 9–12 nucleotides in length. Any RNA molecule with a specific substrate binding site complementary to the intended target and an enzymatic site to effect cleavage is suitable for use with the present invention.

Accordingly, a vector of the invention can contain, for example, an RNA or DNA polynucleotide encoding one or more ribozymes that replicate or are transcribed inside the target cell to produce ribozyme RNAs which then inactivate a desired target RNA sequence. Individuals can be treated using a vector of the invention containing a genetic sequence corresponding to a ribozyme or combination of ribozymes. For therapy of a viral infection such as HCV, a combination of ribozymes specific for different cleavage sites on the viral polynucleotide are preferred. Also preferred are vectors comprising multiple copies of the same ribozyme sequence.

The ribozyme sequence is operably linked in the deleted vector to a suitable promoter, such as a T7 RNA polymerase promoter, that facilitates transcription in the target cell. The expression system of the ribozyme sequence can be constitutive or inducible, but for the treatment of viral infections is preferably constitutive. Ribozymes can be directly transcribed, or alternatively, can be transcribed as part of a larger RNA molecule. Larger RNA molecules can help to stabilize the ribozyme molecules against nuclease digestion within cells. In another example, DNA corresponding to ribozyme sequences can be ligated onto the 3' end of a carrier gene after a translation stop signal. On translation, the 5' encoding region produces a protein that can be directly assayed, for example, by enzymatic reaction or immunohistochemical staining.

Delivering components of heterologous viral systems using vectors of the invention can be used alone or in addition to a sequence with a direct therapeutic effect. Desirable properties of a virus used to construct a viral vector of the invention can include its suitability for the recombination/deletion event, rapid packaging, ability to produce high viral titers, trophism for a particular cell target, ability to deliver a polynucleotide into the target, non-immunogenicity, or suitability for administration to humans. Desirable properties of the virus used to contribute the heterologous sequence can include ability to integrate or undergo long-term replication in the target cell, or its ability to combine with other components in the target to exert a particular effect. Any combination of elements from a plurality of viral systems is provided in the invention.

In some applications, it is desirable to direct the gene therapy to particular tissue types. If the virus is not naturally selective for the intended target, tissue specificity can be imparted by several techniques. In the context of in vivo therapy, a vector of the invention can be provided locally, for example, by direct injection into a tumor site, or by providing an aerosol for lung delivery. Another way to impart tissue specificity upon a vector of the invention is to design the heterologous polynucleotide with a tissue-specific promoter or enhancer.

In other embodiments of the invention, viral vectors for use either ex vivo or in vivo are imparted with a means by which they can home to the intended target tissue. As a consequence, when administered to the recipient or added to an in vitro culture, they accumulate in greater prevalence near certain cell or tissue types than otherwise. This targeting can be effected by providing the composition with a tissue-specific component that reacts with an element at the cell surface or in the vicinity. The component increases the duration during which the vector remains near the target cell or promotes more rapid egress into cells of the desired type.

Suitable targeting components include but are not limited to: surface components that are present on tissue specific viruses or other pathogens, such as the hemagglutinin antigen of influenza, and the F and G glycoprotein of RSV; ligands and ligand analogues for which the target cell has receptors such as cytokines and hormones, adherence proteins like ICAM and ELAM, mediators of endocytosis such as the hepatocyte asialoglycoprotein receptor; isolated naturally occurring recognition units from exogenous sources that are capable of distinguishing between cell types, such as certain plant lectins; and antibodies and antibody equivalents specific for the intended target cell. These include antibodies raised against a cell-surface antigen of the target, antibodies that are specific for a particular autoantigen that is specifically associated within the host with a particular tissue type (such as the CD34 antigen on stem cells), and antibodies directed against tumor-associated antigens like CEA.

Targeting components can be attached to viral vectors of the invention by several approaches known in the art. For example, peptide components can be attached to the viral coat of a virus containing a viral vector using one of the many heterobifunctional cross-linking agents that are available commercially. A preferred method for delivering adenovirus vectors to the liver is to conjugate the vector with an asialoorosomucoid-poly(L-lysine) complex (Cristiano et al., *Proc. Natl. Acad. Sci.* USA 90:11548–11552 (1993)).

Alternatively, the targeting component or a binding unit can be engineered into a viral package. In one example, a gene encoding a surface component of the adenovirus vector, such as the fiber, is modified to encode a fusion protein containing such targeting elements as RSV glycoproteins, gp160, and TSH. In another example, a gene for a viral surface component is modified to encode a fusion protein comprising a binding site from avidin or the Fc binding region of protein A. A packaged virus bearing such fusion proteins would subsequently be capable of binding biotin-conjugated targeting components and specific antibodies, respectively. Modification of the appropriate encoding region can be performed at the level of the plasmid constructs used to generate the precursor vectors of the invention. The package of the precursor vector would thereafter contain the fusion protein, as would the deleted vector subsequently obtained.

Vectors embodied in the invention can be used for gene therapy of an individual. Methods of gene therapy are described generally in Anderson et al. (U.S. Pat. No. 5,399, 346). For purposes of therapy, cells can be genetically altered either ex vivo or in vivo.

To conduct gene therapy ex vivo, cells are removed from a donor (or obtained from a cultured cell line), genetically altered with a deleted viral vector, and then administered to a recipient. The cells are obtained from the donor in the form of a blood sample, bone marrow aspirate, biopsy, surgical excision, or other clinically suitable procedure. The cells are optionally purified or otherwise subfractionated, and then treated with a vector of the invention containing a heterologous polynucleotide therapeutically directed at a pathological condition in the intended recipient. After transduction, the cells are optionally cultured or otherwise manipulated, and then administered to the recipient. Preferably, the cell donor is the same as the recipient of the transduced cells (an autologous transplant). However, the transfer of cells from one individual to another is permissible, or even preferred where the recipient does not have sufficient donor cells for autologous treatment. The donor is preferably histocompatible and blood group identical or compatible with the recipient, although this can be less important for administration of cells that are normally immunologically privileged, such as those in the liver. In principle, ex vivo gene therapy can be conducted on any cell type which can be obtained and manipulated in vitro in sufficient quantity.

One example of ex vivo gene therapy is conducted on stem cells, obtained either from bone marrow or peripheral blood, such as CD34+ cells. This can be undertaken, for example, to treat an individual with a congenital deficiency affecting hematopoiesis, in which case the therapeutic gene is intended to correct the metabolic deficiency. It can also be undertaken to confer upon certain cell types a novel function; for example, lymphocytes can be conferred with an ability to recognize additional foreign antigens or additional autologous cell-surface receptors, immune recognition units, cytokines, or adhesion proteins. In patients that have been depleted of hematopoietic cells, for example, by irradiation, chemotherapy, or by infection, transplanted cells can be treated with heterologous polynucleotides, for example, to confer enhanced tumor suppression activity, or ensure that they are free of active components of the etiologic agent.

Another illustration of ex vivo gene therapy is performed on hepatocytes. This can be undertaken, for example, to treat an individual with a congenital deficiency affecting any metabolic property normally exercised by the liver, or any congenital deficiency that is correctable by conferring the missing metabolic property on the liver, such as one that affects blood chemistry. It can also be undertaken to replace virally infected or cancerous hepatocytes with unaffected hepatocytes.

To conduct gene therapy on hepatocytes ex vivo, hepatocytes are removed from the individual, typically by surgical or biopsy means. Although a small amount of hepatocytes is usually sufficient, about $1 \times 10^7$, sometimes about $1 \times 10^8$, sometimes about $1-5 \times 10^9$ cells, or up to 20% or more (but desirably less) of the patient's liver can be removed and serve as a source of cellular material. The hepatocytes are generally obtained from a tissue sample by separating the cells by such enzymes as collagenase that degrade the matrix surrounding the cells. Preferably, hepatocytes are separated from other liver cells, such as Kupffer cells and endothelial cells. The hepatocytes are then cultured or otherwise prepared for transduction by a vector which contains a gene that expresses the gene product of interest. The transduced hepatocytes can be cultured for up to 5 to 10 days or longer to obtain sufficient numbers of cells for administration. Typically, the cells will be returned to the individual by infusion via the portal or splenic vein, in single or multiple administrations, if possible beginning within about 1–5 days after removal.

The effectiveness of the genetic alteration can be monitored by determining whether the cells express the function intended to be conveyed by the therapeutic polynucleotide. Suitable methods include Northern analysis and solution hybridization of mRNA obtained from the cells, in situ hybridization, immunohistology, and immunofluorescent cell counting. Preferably, at least 20% of the target cell population within the mixture of donor cells are modified to express the desired function, with higher percentages being increasingly more preferred. If desired, the cell population can be subjected to multiple rounds of alteration and analysis before administration to the recipient.

If it is intended that the genetically altered cells replace native cells in the recipient, it can be desirable to treat the recipient to enhance replacement. Suitable treatments can include chemical or gene therapy techniques, radiation, or other clinical regimens that are focused on the target tissue. The treatment is generally undertaken between the time when the donor cells are collected from the individual, and the time when they are readministered after modification, although other variations can be used. The treatment can be toxic for the unaltered cells, or it can promote regeneration of altered cells or replacement of unaltered cells without killing.

One illustration is the treatment of hepatocellular disease, wherein donor hepatocytes are modified by ex vivo gene therapy, and liver cells in vivo are treated to render them susceptible to replacement. Prior to reinfusing the ex vivo modified hepatocytes, the patient is infected with a viral vector which encodes a hepatotoxic protein capable of inhibiting or slowly killing hepatocytes. Typically the hepatotoxic protein is one such as urokinase-type plasminogen activator (uPA), or the protein can be tissue-type plasminogen activator (tPA), which can stimulate hepatocyte regeneration de novo, without causing liver damage. The viral vector is preferably hepatotropic. The hepatotoxin should be specific for hepatocytes, or if not specific, should not be secreted in substantial amounts by the infected hepatocytes into the bloodstream. A representative example is uPA that has been modified at the N-and/or C-terminal to inhibit secretion by the altered cell. Other toxins such as are listed elsewhere in this disclosure can be used, and are preferably placed under the control of a liver-specific promoter.

Vectors embodied in the invention can also be used for administration directly to an individual for purposes of gene therapy in vivo. Suitable diseases include but are not limited to those induced by viral, bacterial, or parasitic infections, various malignancies and hyperproliferative conditions, autoimmune conditions, and congenital deficiencies. Non-limiting examples of genes and vectors useful for treating such conditions are listed elsewhere in this disclosure. Selection of a therapeutic gene appropriate for a particular condition has been outlined in an earlier section.

For general systemic administration of a vector required at a particular tissue site, vectors containing a tissue-specific promoter or a tissue targeting component are preferred. The viral vector is administered in an amount effective to the subject. Generally, dosage will approximate that which is typical for the administration of nucleic acids, particularly (in the case of adenovirus vectors) those that remain extra-chromosomal.

What constitutes an effective amount depends on the condition of the recipient and the objective of treatment. The vector particles can be administered in an amount from 1 plaque forming unit to about $10^{14}$ plaque forming units, more usually from about $1 \times 10^6$ plaque forming units to about $1 \times 10^{13}$ plaque forming units. Where a low percentage of transduction can cure a genetic deficiency, then the objective of treatment is generally to meet or exceed this level of transduction. In some instances, this level of transduction can be achieved by transduction of only about 1 to 5% of the target cells, especially if the gene is normally expressed by a small proportion of cells or at a modest level, or if the therapeutic gene is provided under control of a more active promoter. In other instances, the treatment will provide a better degree of protection or a longer lasting effect if a large percentage of cells in the target tissue are modified. In these instances, a sufficient number of vector particles should be administered preferably to infect at least about 20% of the cells of the desired tissue type, generally at least about 50%, usually at least about 80% to at least about 95%, and preferably at least about 99% of the cells of the desired tissue type. The treatment can be repeated as required.

When the treatment is aimed at cancerous or virally infected cells, then an objective of treatment is typically to modify all such affected cells. Thus, a sufficient number of vector particles should be administered preferably to infect at least about 50% of cells of the desired tissue type, generally at least about 80%, usually at least about 95%, and preferably at least about 99% of the affected cells. Typically, from about 1 to about 100 infectious virus particles are administered per cell; more typically about 10 infectious particles are administered per cell. Multiple administrations can be undertaken to increase the proportion of treated cells, to increase the number of copies of therapeutic polynucleotide per cell, or to maintain the modification where it is desired that the effect be maintained for an extended time.

The effectiveness of the genetic alteration can be monitored by determining whether the cells express the function intended to be conveyed by the therapeutic polynucleotide. Samples removed by biopsy or surgical excision can be analyzed by in situ hybridization, immunohistology, or immunofluorescent cell counting. Preferably, at least 20% of the target cell population within the mixture of donor cells express the desired function, with higher percentages being increasingly more preferred. If the genetic alteration is expected to affect the composition of blood, then this generally provides a more convenient method of measuring effectiveness. Therapy for $\alpha_1$-antitrypsin or Factor IX deficiency should elevate the level of these proteins in serum, which can be measured by standard immunoassay. Therapy for Hepatitis B or C infection should result in a decrease in serum levels of associated markers, determined by immunoassay or hybridization assay. Ultimately, the effectiveness of the therapy is assessed by an improvement in the clinical symptoms of the affected individual.

Embodied in this invention are pharmaceuticals containing vectors with at least one heterologous polynucleotide of therapeutic interest. As described elsewhere in this disclosure, vectors for in vivo use are preferably replication-defective, and preferably non-immunogenic.

Vectors are prepared for administration to an individual in need thereof, including humans, in accordance with generally accepted procedures for the preparation of pharmaceutical preparations. See, for example, Remington's Pharmaceutical Sciences, E. W. Martin ed., Mack Publishing Co., PA. Depending on the intended use and mode of administration, it can be desirable to process the vector particles further in the preparation of pharmaceutical compositions. Appropriate processing can include sterilizing, mixing with appropriate nontoxic and non-interfering components, dividing into dose units, and enclosing in a delivery device.

Pharmaceutical compositions of the invention minimally comprise a therapeutically effective vector, which can be combined with a pharmaceutically acceptable excipient. Liquid pharmaceutically administrable compositions can, for example, be prepared by dissolving or dispersing a vector embodied herein in a liquid excipient, such as water, saline, aqueous dextrose, glycerol, or ethanol. The composition can optionally also contain other medicinal agents, pharmaceutical agents, adjuvants, carriers, and auxiliary substances. Conventional nontoxic carriers include pharmaceutical grades of mannitol, lactose, starch, magnesium stearate, sodium saccharin, talk, cellulose, glucose, sucrose, and magnesium carbonate. Nontoxic auxiliary substances include wetting or emulsifying agents, and pH buffering agents such as sodium acetate, sodium or potassium phosphate, sorbitan monolaurate, triethanolamine sodium acetate, and triethanolamine oleate.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides either a solid or liquid aerosol when used with an appropriate aerosolizer device. Although not required, pharmaceutical compositions are preferably supplied in unit dosage form suitable for administration of a precise amount. Also contemplated by this invention are slow release or sustained release forms, whereby a relatively consistent level of the active component is provided on an ongoing basis over an extended period.

The route of administration of a pharmaceutical composition depends on the intended target site and the viral species from which the therapeutic vector is derived. In general, the route is expected to be similar to that described for delivery of other vectors. Suitable routes can include parenteral, intramuscular, subcutaneous, intradermal, intravenous (including via an indwelling catheter), oral, intraperitoneal, intranasal, and by inhalation. In certain instances, it is preferable to inject the composition directly into a pathologically affected tissue site. In other instances, particularly when the vector is tropic for the intended target site or comprises tissue-specific controlling elements, systemic administration is sufficient. Typically, intravenous or inhalation administration is preferred.

The decision of whether to use in vivo or ex vivo therapy, and the selection of a particular composition, dose, and route of administration will depend on a number of different factors, including but not limited to features of the condition being treated, such as location and genetic basis, and features of the subject being treated, such as age, weight, and clinical condition. The assessment of such features and the design of an appropriate therapeutic regimen is ultimately the responsibility of the prescribing physician.

It is understood that modification which do not substantially affect the activity of the various embodiments of this invention are also provided within the definition of the invention provided herein. Accordingly, the following examples are intended to illustrate but not limit the present invention.

EXAMPLE I

Trans-complementation with First Generation Adenovirus Confers Stability on Adenoviral Mini-vector This example demonstrates that first generation adenovirus confers stability on adenoviral mini-vector DNA deleted of the region containing the genes for E2 proteins.

Female C57B1/6 mice (Jackson Labs, Bar Harbor, Me.) aged 5 to 6 weeks were used in the described experiments. Adenovirus injections were performed by tail vein infusions with 200 µl of virus diluted in adenovirus storage buffer. Generally, $5 \times 10^9$ transducing particles were injected per mouse, a dose that transduces ~95% of hepatocytes. Blood samples for hAAT or SGPT analysis were obtained by retroorbital or tail vein bleeding, respectively. hAAT concentrations in serum or tissue culture samples were measured by ELISA (Kay et al., Hepatology 21:815–819 (1995)). A diagnostic kit (Sigma, St. Louis, Mo.) was used for calorimetric determination of the activity of SGPT with 10 µl serum (Lieber et al, Hum. Gene Ther. 6:5–11 (1995)).

Coinfection studies strongly suggested that trans-acting, viral factor(s) missing in the deleted vector play a role in viral genome persistence (Lieber et al., J. Virol. 70:8944–8960 (1996)). To further elucidate this in animals, different amounts of E1 deleted Ad.RSVβgal were added as helper to $5 \times 10^9$ transducing particles of ΔAd.hAAT (deleted vector) prior to intravenous infusion into C57B1/6 mice. In mice receiving ΔAd.hAAT alone or with $5 \times 10^6$ (0.1%) transducing particles of Ad.RSVβgal, serum hAAT were only detectable for less than 5 days. In contrast, mice that received as little as 1% helper ($5 \times 10^7$ transducing particles) expressed hAAT for more than 2 months, similar to the length of beta-gal expression in these mice. At a dose of $5 \times 10^9$ transducing particles (MOI estimated at 50 with $1 \times 10^8$ hepatocytes per liver) about 15 to 30 adenoviral genomes were found in hepatocytes transduced in vivo. Thus with 1% of this amount added as helper, we estimate about 1 helper vector genome for every 2 to 3 hepatocytes.

These results show that the first generation virus contains one or more components which stabilize vector DNA in trans.

EXAMPLE II

Transient pTP Coexpression Stabilities ΔAd.hAAT Genomes In Vitro

This example demonstrates that pTP expression stabilizes an adenoviral vector deleted of the E2 region.

The effect of transient expression of the E2 proteins pTP, polymerase (pol) and DBP on the stability of ΔAd.hAAT was measured in vitro. $5 \times 10^5$ HeLa cells were transfected with a total of 10 µg plasmid. The amount of the specific plasmid, pCMV pTP (pTP), pCMVpol (pol) or pBZ20 (DBP) was 3.3 µg per transfection. To obtain the total concentration of 10 µg plasmid, control DNA (pCDNA3) was added. Thirty six hours after transfection, ΔAd.hAAT at an moi of 50 was added to the cells that had reached confluence at this time point ($2 \times 10^6$ cells per 6 cm dish) Co-all transfected DNA was pCDNA3. In FIG. 1, Part A, cell culture medium (5 ml) was changed daily and hAAT concentration analyzed by ELISA. (n=3) per time point and the variation was less than 10% at each point. In FIG. 1, Part B, one set of cells was harvested at 5 hours post infection with ΔAd.hAAT, another set was collected at day 7 post-infection for DNA analysis. 10 µg genomic DNA digested with BamHI was analyzed by Southern blotting for viral DNA using a P-labelled hAAT probe. The specific band was 2.0 kb. The hybridization signal was quantified by phosphoimager-analysis after adjusting for loading differences. The data are expressed as arbitrary units relative to a concentration standard loaded on the gel.

$5 \times 10^3$ HeLa cells in 6 cm dishes were transfected by Ca-phosphate coprecipitation. Generally, the transfection efficiency was ~50% as determined by X-Gal staining after transfection with 10 µg pCMV β-Gal. The plasmids pCMVpTP, pCMVpol or pBZ20 (DPB) were transfected separately or in combination in two sets of dishes in a total of 10 µg/dish. ΔAd.hAAT (moi 100) was added 36 h after transfection. At this time, cells had reached confluence. A plasmid with the CMV-promoter, but without the pTP gene (pDNA3, Invitrogen) was used as control in cotransfection experiments.

At different time points after plasmid transection, cell pellets were lysed on ice for 30 min in 20 mM HEPES pH7.5, 2 mM EGTA, 10% glycerol, 1% Triton X-100, 0.1 M DTT and protease inhibitors. After 5 min boiling, 100 µg total protein in 1×Laemmli buffer with 4% β-mercaptoethanlol, proteins were separated on a 10% SDS-PA (polyacrylamide) gel. After electrotransfer and blocking, filters were incubated with monoclonal anti-pTP antibodies (1:40 diluted) or anti-DBP antibodies (1:50 diluted, Mab 37-3, GenVec), followed by an incubation with peroxidase-labelled anti-mouse Ig antibodies (1:1000). Filters were developed using the ECL detection kit (Amersham).

For genomic DNA preparations, cultured cells were washed three times with PBS before harvesting mouse livers were flushed with 5 ml PBS via the portal vein. Genomic DNA was extracted from 100 mg liver as described in. For preparation of nuclear DNA nuclei were isolated and purified by a procedure published in. For analysis, 100 µof genomic DNA was digested with BamHI, run on a 0.8% agarose gel, and electrotransfered to Hybond nylon filters (Amersham). The blots were hybridized in rapid hybridization buffer (Amersham) with [α-P]dCTP-labelled DNA probes. As reference standard, DNA from noninfected cells or livers was spiked with 5 pg of deleted viral genomic DNA and loaded on each gel. The relative amount of adenovirus DNA was determined by Phosphorimager analysis as a ratio between the sample signal and the standard signal, and expressed as arbitrary units. All blots were rehybridized with probes for the mouse metallothionein gene (mouse liver DNA) or for the genomic hAAT gene (HeLa DNA) to adjust load mg differences. The following DNA fragments were used as labelled probes: 1.4 kb of the hAAT cDNA (EcoRI fragment of pAd.RSVhAAT, 3.6 kb probe of pTP DNA (HindIII/EcoRI fragment of pCMVpTP) or 2 kb fragment of the mouse MT gene (HindIII/EcoRI fragment of pmMMT).

For pTP detection after in vivo transduction with ΔAd.pTP, livers were first flushed with 5 ml PBS via the portal vein then 300 mg tissue was homogenized in 1 ml RIPA (PBS, 1% NP40, 0.5% sodium deoxycholat, 0.1% SDS, protease inhibitors) and incubated for 30 min on ice. After adding $MgCl_2$ to a final concentration of 5 mM, cell lysates were incubated with 20 μg/ml DNaseI for 30 min at room temperature. Lysates with a total of 12 mg protein were incubated with anti-pTP antibodies (1:40) overnight at 4° C., followed by an incubation with protein-A SEPHAROSE (Sigma) for 1 h at 4° C. After 4 times washing with RIPA, SEPHAROSE bead pellets were resuspended in an equal volume of 2×Laemmli buffer with 8% β-mercaptoethanol and boiled for 5 min before loading on a 10% PA gel.

Elements in the helper virus that provide stabilization of the deleted genome could represent the helper genome itself or early/late proteins expressed from this genome. The nuclear-localized, DNA-binding proteins encoded in the E2 region (pTP, DBP, pol) were tested to determine if they would provide the stabilization of the deleted genome when transiently expressed (separately or in combination) prior to transduction with ΔAd.hAAT. To do this, expression plasmids with the individual E2 genes, pTP, DNA binding protein or polymerase individually or in combination were cotransfected onto $5 \times 10^5$ cells, and 36 hours later cells were transduced with ΔAd.hAAT (FIG. 1). Expression studies with specific antibodies (immunofluorescence or Western blot) demonstrated detectable pTP or DBP expression between 24 hours and 7 days after plasmid transfection. The expression of pTP alone or in combination with pol stabilized and enhanced hAAT gene expression for at least 6 days, whereas hAAT levels from cells transfected with a control plasmid declined over the analyzed time period of 6 days after transduction with ΔAd.hAAT (FIG. 1a). DBP expression inhibited hAAT expression from the transduced vector, probably due to negative effects on cell viability. The amount of vector DNA isolated from the transduced cells monitored at 5 hours (input) and 7 days correlated well with hAAT expression levels (FIG. 1b). pTP-expressing cells had even a slightly higher concentration of vector DNA at 7 days compared with the input measured at 5 hours. One possible explanation is that high level pTP expression prior to vector transduction influenced nuclear transport at time points after 5 h post-infection with ΔAd.hAAT. In contrast, in transduced cells where pTP expression was absent, by 7 days the amount of deleted genomes was significantly reduced compared with the concentration of input DNA.

These results show that coexpression of pTP stabilizes deleted adenoviral DNA lacking the E2 region.

EXAMPLE III

The pTP Mini-vector Confers Self-stability and Stability of Another Coinfected Deleted Vector This example demonstrates that pTP can stabilize vector DNA in cis and in trans.

The generation of the deleted adenovirus containing the hAAT expression cassette (ΔAd.hAAT) was carried out as described (Lieber et al., supra, 1996). To produce ΔAd.pTP the plasmids pAd.pTPlox and pBHGlllOX were cotransfected into 293 cells to generate recombinant virus containing two lox sites. Recombinant vector from single plaques was amplified in 293 cells and analyzed for pTP expression by Western Blot with monoclonal antibodies against pTP (obtained from Dr. Sarah Jones, University of St Andrews, England). The intensity of the specific 80 kD pTP-band from vectors with exogenous pTP expression was ~20-fold stronger than the pTP band derived from endogenous pTP expression in first generation adenoviruses. Virus from positive plaques was amplified in large scale in 293 cells infected with an moi (multiplicity of infection) of >200. To generate deleted virus expressing pTP (ΔAd.pTP), the vector containing the two lox sites was infected onto 293 cells expressing cre recombinase (293-cre) at an moi of 200. Cre mediated the efficient excision of the intervening 25 kb region, joining the left genome end, with ITR and the RSV-hAAT-bPA cassette and the right genome end with the E4 region and the right ITR together. Infected 293-cre cells were harvested at 48 h pi (post infection) and deleted virus was banded by multiple rounds of CsCl ultracentrifugation as described earlier.

Titers given in transducing particles of ΔAd.hAAT or ΔAd.pTP were determined on HeLa cells by immunofluorscence using antibodies specific to E4 proteins (rabbit anti ORF-3 and anti-ORF4, 1:1 mixture, provided by Dr. Gary Ketnar, Johns Hopkins University). All preparation of deleted viruses were tested for contaminating first generation adenovirus (with two lox sites) by plaque assay On 293 cells. Only preparations with fewer than 5 plaques per $10^6$ transforming units (less than 0.0005% contamination) were used in the experiments. Viruses were stored at a titer of $3 \times 10^{10}$ transducing particles at −80° C. in 10 mM Tris-Cl, pH8.0, 1 mM $MgCl_2$ and 10% glycerol.

Analysis of viral DNA after transduction in vitro with ΔAd.hAAT and ΔAd.pTP was performed. Confluent HeLa or BHK cells were transduced in vivo with deleted vectors (moi 100). Five hours or 7 days after infection cells were harvested, and genomic DNA digested with BamHI was analyzed by Southern blotting with a $^{32}P$-labelled hAAT or pTP probe. The BamHI fragment specific for viral DNA was 2.0 kb for ΔAd.hAAT and 3.6 kb for ΔAd.pTP. Confluent HeLa cells were transduced with deleted vectors and specific viral DNA was quantitated in nuclear DNA from cells collected at 1 h, 5 h, or 24 hours post infection.

Analysis of viral DNA after transduction in vivo with ΔAd.hAAT and ΔAd.pTP was performed. C57B1/6 mice were injected with $5 \times 10^9$ infectious particles of ΔAd.hAAT or ΔAd.pTP. At 1 hour or 21 days after virus infusion genomic liver DNA was analyzed for specific viral DNA using $^{32}P$-labelled hAAT- or pTP probe. The results from 4 different mice per time point are shown in FIG. 3. The specific bands were 2.0 and 3.6 kb for viral DNA and ΔAd.hAAT, respectively.

Figure 4A:
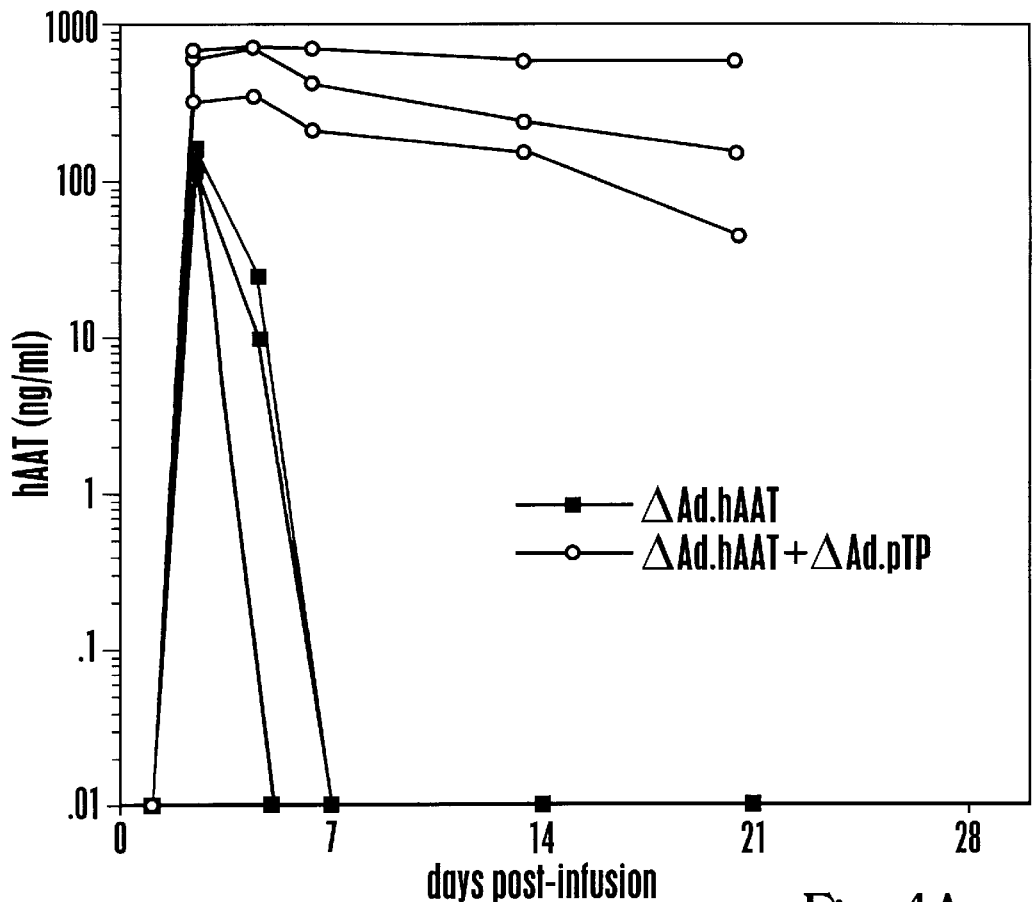
FIGS. 4A and 4B show combined infusion of ΔAd.hAAT and ΔAd.pTP. Part A shows serum hAAT levels. Part B shows viral DNA at day 1 and day 21.
Figure 4B:
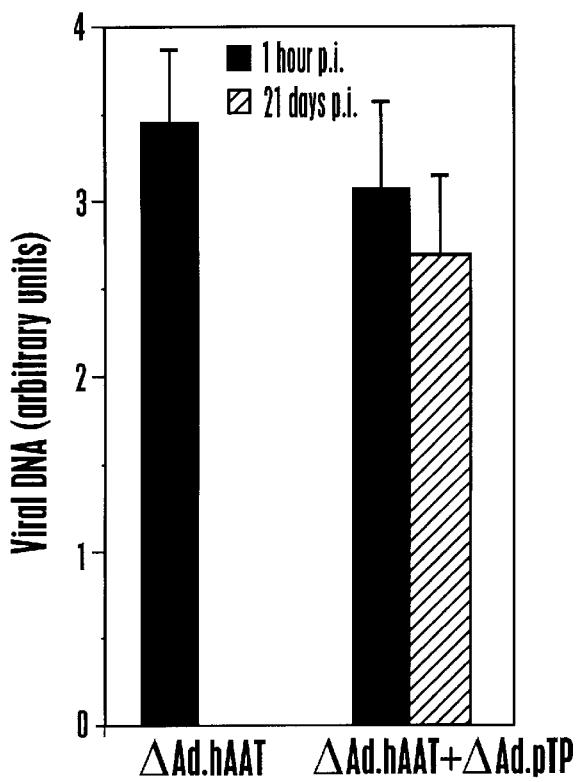

Combined infusion of ΔAd.hAAT and ΔAd.pTP was performed. $5 \times 10^9$ transducing particles of ΔAd.hAAT alone or ΔAd.hAAT in combination with $5 \times 10^9$ transducing particles of ΔAd.pTP was infused in C57B1/6 mice. FIG. 4A shows serum hAAT levels. FIG. 4B shows genomic liver DNA at day 1 and day 2 was isolated for quantitation of viral DNA by Southern analysis using a hAAT specific probe. n=3 per group.

A second deleted vector, ΔAd.pTP (9 kb) containing the pTP gene in place of the hAAT cDNA was constructed (FIG. 2) in order to determine whether pTP expression can self-stabilize ΔAd.pTP or ΔAd.hAAT when coinfected. To produce ΔAd.pTP, first, vectors with two lox sites flanking the pIX and E2 regions were generated by recombination of pAd.pTPlox with pBHGlox1 with the lox site cloned into the E3 region, then these vectors were infected into 293-cre cells to delete the intervening region between the lox sites. The resulting deleted vectors had approximately the same size (~9 kb).

Western Blot analysis on liver extracts or cultured cells transduced with ΔAd.pTP revealed the 80 kDa pTP-protein. Notably, the 80 kDa pTP specific band was also detected in livers transduced with a first generation adenovirus (Ad.RSVhAAT), demonstrating that pTP is expressed from first generation vectors in hepatocytes in vivo.

The ΔAd.pTP vector genome was stable after transduction into cultured HeLa and BHK cells for at least a week whereas by 24 hours ΔAd.hAAT vector DNA transduced in parallel experiments declined to very low levels. To prove that the viral DNA detected at the early time points truly represented DNA transported to the nucleus and not unstable, non-transducing DNA/viral particles contained in the cytoplasm or membrane, Southern analysis was performed at the early time points with genomic DNA isolated from purified nuclei. As expected based on the comparable early concentrations of hAAT expression from both first generation and deleted vectors, the majority of deleted vector DNA was in the nucleus prior to its disappearance. This excludes the possibility that pTP expressed from deleted genomes that reached the nucleus significantly facilitates the nuclear transport of vector DNA still remaining in the cytoplasm. Taken together, a deleted adenoviral vector genome can be stabilized in the nucleus of cells in culture when pTP is expressed from the vector.

Similar results to those obtained in cell culture were achieved in animals infused with deleted vector expressing pTP (FIG. 3). ΔAd.pTP transduced mouse livers had only slightly reduced amounts of vector DNA at 21 days (the length of the experiment) compared to 1 hour p.i., while similar to previous results, the ΔAd.hAAT vector was undetectable by 7 days. In the next set of experiments, the ΔAd.hAAT and ΔAd.pTP virus were mixed prior to infusion into mice to determine if trans-complemenation would stabilize the genome and transgene expression (FIG. 4). Mice receiving both vectors had stable serum hAAT expression (FIG. 4a) and persistence of both vector genomes (FIG. 4b) for at least three weeks, whereas mice receiving ΔAd.hAAT alone had transient serum hAAT levels as well as vector DNA.

These results show that pTP stabilizes vector DNA for up to 7 days when the pTP gene is provided in cis or in trans.

EXAMPLE IV

Toxicity of pTP Expression In Vivo

This example demonstrates that pTP expression is non-toxic in animals.

SGPT levels in mice infused with first generation adenovirus hAAT, ΔAd.hAAT, or ΔAd.pTP. SGPT levels were determined periodically after intravenous infusion of $5 \times 10^9$ transducing particles n=3 per time point.

To determine if pTP expression in vivo was associated with liver toxicity, serum levels of glutamic pyruvic transaminase (SGPT), an early and sensitive marker for hepatocellular injury, were measured in animals transduced with ΔAd.pTP and found to be only slightly higher than those from mice receiving ΔAd.hAAT (FIG. 5). Based on these studies, the level of pTP expression from ΔAd.pTP does not appear to be toxic in vivo. Taken together, expression of pTP-protein in trans or cis results in stabilization of E2 deleted adenoviral genomes in vivo without obvious toxic side effects.

These results show that pTP does not induce liver toxicity in mice expressing pTP.

EXAMPLE V

Increased Nuclear Import of Vector DNA Mediated by pTP

This example demonstrates increased nuclear transport of vector DNA by pTP.

A fragment of Ad5 DNA (0.8 kb of pFG140; bp: −382 to +452) containing two head to head joined adenoviral ITRs was used as pTP binding domain. This fragment was cloned in front of a hAAT expression cassette (pITR-hAAT) (provided by J. Nelson) (see FIG. 6). phAAT containing the same expression cassette but without the ITRs was included in all transfections as control.

The following transfection scheme was used to assess whether pITR-hAAT transport into the nucleus of arrested cells could be restored by pTP coexpression. Briefly, BHK cells 90% confluent were transfected with pCMV or pCMVpTP (time 0). In scheme A, cells were transfected with phAAT or pITR-hAAT at 36 h when cells were 100% confluent, and nuclear genomic DNA was extracted at 60 h. In scheme B, cells were treated with 10% fetal calf serum±HU (hydroxyurea) or with serum-free media±HU at 36 h when cells were 100% confluent. At 5 days, cells were transfected with phAAT or pITR-hAAT and nuclear genomic DNA was extracted at day 6.

Two sets of cell culture dishes (A and B) were transfected with pCMV or pCMVpTP. In protocol A, the test plasmids (phAAT, pITR-hAAT) were transfected when pTP was already produced but all cells were still dividing (36 h). Twenty four hours after adding the test plasmids, cells were carefully washed, lysed with NP40, and genomic DNA was extracted from purified nuclei. In protocol B, cells expressing pTP were arrested in cell cycle and transfected with the test plasmids. Cells were harvested as in protocol A and nuclear DNA was extracted. Transfected plasmid DNA was quantified after Southern blot of genomic nuclear DNA with a hAAT probe (detecting a 1.7 kb band). After quantitation on a phosphoimager, the ratio of plasmid concentration obtained in protocol A and B was used to express the effect of pTP mediated nuclear transport (see FIG. 7).

FIG. 7 clearly shows that nuclear import of pITR-hAAT in arrested BHK cells is efficient only when pTP was coexpressed and that this effect was specific for plasmids carrying the pTP binding domain.

These results show that pTP enhances nuclear import of DNA containing a pTP binding domain.

EXAMPLE VI

Enhanced Stabilization of Retroviral DNA by Adenoviral pTP

This example demonstrates the ability of pTP to enhance nuclear transport and stabilize retroviral DNA.

To generate retroviral vectors containing pTP binding domains, constructs containing two adenoviral ITRs and the hAAT cDNA were generated based on MSCV vector (Hawley et al.) (see FIG. 8). Two different positions for pTP cloning (pRV.ITR-hAAT, pRV.hAAT-ITR) were chosen.

These constructs are cotransfected with pSV2neo in ecotropic retrovirus packaging cell lines, and after G418 selection, retrovirus pools are tested for hAAT transduction and titered by hAAT immunofluorescence in transduced cells. Then, amphotropic packaging cell lines are infected, and clones with high titer retrovirus production are isolated.

Initial transduction experiments are carried out with ecotropic virus pools (RV-ITR-hAAT) on arrested BHK cells expressing stable pTP (pMTpTP). hAAT levels in the culture supernatants are monitored. Extrachromosomal retroviral-hAAT DNA and integrated hAAT DNA are quantified by Southern blot at different time points after retrovirus infection. Other cell types, for example, nondividing primary mouse hepatocytes and peritoneal macrophages, are also transduced with the retroviral vectors. Prior to retrovirus (RV-ITR-hAAT) exposure, the primary cells are transfected with pCMVpTP or infected with Ad.pTP. The effect of multiple exposures to retrovirus (RV-ITR-hAAT) to pTP expressing quiescent cells are determined.

These results show that pTP can be used to stabilize retroviral DNA containing pTP binding domains.

Throughout this application various publications have been referenced within parentheses. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed is:

1. A non-adenoviral vector comprising a polynucleotide sequence encoding adenoviral pTP operationally linked to an expression element and an adenoviral ITR or functional fragment thereof comprising an adenoviral pTP binding domain.

2. The non-adenoviral vector of claim 1, further comprising a polynucleotide of interest operationally linked to an expression element.

3. The non-adenoviral vector of claim 1, wherein said vector is selected from the group consisting of retroviral DNA, herpesviral DNA, poxviral DNA, DNA vectors, pseudotype retroviral vectors, adeno-associated virus, gibbon ape leukemia vector, vesicular stomatitis virus-G, and VL30 vectors.

4. The non-adenoviral vector of claim 1, wherein said vector is in a liposome.

5. A composition comprising adenoviral pTP and a non-adenoviral vector containing an adenoviral pTP binding domain.

6. The composition of claim 5, further comprising a viral particle.

7. The composition of claim 5, further comprising a liposome.

8. An in vitro method of increasing the expression of a polynucleotide, comprising expressing a non-adenoviral vector comprising said polynucleotide and an adenoviral ITR or functional fragment thereof comprising an adenoviral pTP binding domain in the presence of adenoviral pTP, thereby increasing expression of said polynucleotide relative to a vector comprising said polynucleotide and lacking an adenoviral pTP binding domain.

9. The method of claim 8, wherein said increased expression comprises an increased time period of expression.

10. The method of claim 8, wherein said increased expression comprises an increased amount of a polypeptide encoded by said polynucleotide.

11. The method of claim 8 wherein said non-adenoviral vector is expressed in a primary cell.

* * * * *

UNITED STATES PATENT AND TRADEMARK OFFICE
CERTIFICATE OF CORRECTION

PATENT NO. : 6,132,989
DATED : October 17, 2000
INVENTOR(S) : Kay et al.

It is certified that error appears in the above-identified patent and that said Letters Patent is hereby corrected as shown below:

Column 20,
Line 57, please delete "100 $\mu$of" and replace with --10 $\mu$g of --.

Signed and Sealed this

Twenty-second Day of June, 2004

JON W. DUDAS
*Acting Director of the United States Patent and Trademark Office*